(12) United States Patent
Ehring et al.

(10) Patent No.: US 7,763,651 B2
(45) Date of Patent: Jul. 27, 2010

(54) TREATING PAIN USING SELECTIVE ANTAGONISTS OF PERSISTENT SODIUM CURRENT

(75) Inventors: George R. Ehring, Huntington Beach, CA (US); Joseph S. Adorante, Irvine, CA (US); John E. Donello, Dana Point, CA (US); Larry A. Wheeler, Irvine, CA (US); Thomas Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 941 days.

(21) Appl. No.: 11/461,520

(22) Filed: Aug. 1, 2006

(65) Prior Publication Data

US 2006/0264503 A1    Nov. 23, 2006

Related U.S. Application Data

(62) Division of application No. 10/928,964, filed on Aug. 27, 2004, now Pat. No. 7,125,908.

(60) Provisional application No. 60/498,900, filed on Aug. 29, 2003.

(51) Int. Cl.
| | |
|---|---|
| *A01N 37/00* | (2006.01) |
| *A01N 37/18* | (2006.01) |
| *A01N 35/00* | (2006.01) |
| *A61K 31/21* | (2006.01) |
| *A61K 31/16* | (2006.01) |
| *A61K 31/12* | (2006.01) |

(52) U.S. Cl. ............... 514/506; 514/510; 514/613; 514/675; 514/678; 514/679; 514/680

(58) Field of Classification Search ............ 514/646, 514/506, 510, 613, 675, 678, 679, 680
See application file for complete search history.

*Primary Examiner*—Yong S Chong
(74) *Attorney, Agent, or Firm*—Dean G. Stathakis; Joel B. German; Allergan, Inc.

(57) ABSTRACT

The present invention provides methods of treating chronic pain in a mammal by administering to the mammal an effective amount of a selective persistent sodium channel antagonist that has at least 20-fold selectivity for persistent sodium current relative to transient sodium current.

50 Claims, 8 Drawing Sheets

| Compound ID | Molecular Formula | MW | Structure | IC50 (P), mM | IC50 (T), mM | Selectivity |
|---|---|---|---|---|---|---|
| Compound 1 (Formula 1) | C15H17NOS | 259.37 | 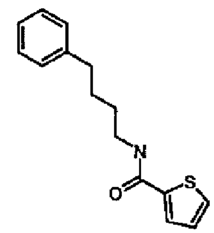 | 0.09 | 2.9 | 32 |
| Compound 2 (Formula 2) | C21H18N3O | 328.40 | 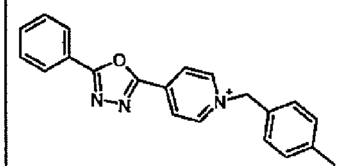 | 0.42 | 16 | 38 |
| Compound 3 (Formula 3) | C27H33NO2 | 403.57 | 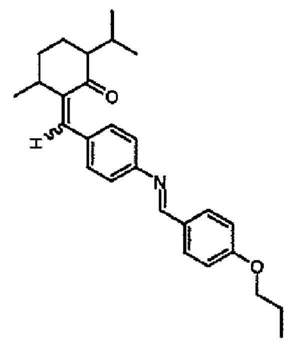 | 0.9 | 408 | 453 |
| Compound 4 (Formula 4) | C17H12NO4F3 | 351.28 | 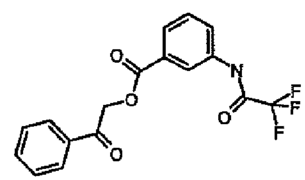 | 0.24 | 26.4 | 110 |

Fig. 1

TREATING PAIN USING SELECTIVE ANTAGONISTS OF PERSISTENT SODIUM CURRENT

CROSS REFERENCES TO RELATED APPLICATIONS

This application is a divisional and claims priority pursuant to 35 U.S.C. §120 to U.S. patent application Ser. No. 10/928,964, filed Aug. 27, 2004 now U.S. Pat. No. 7,125,908, an application that claims priority pursuant to 35 U.S.C. §119(e) to provisional application Ser. No. 60/498,900 filed Aug. 29, 2003, both of which are hereby incorporated by reference in their entirety.

BACKGROUND OF THE INVENTION

1. Field of the Invention

This invention relates generally to the fields of neurobiology, physiology, biochemistry and medicine and can be directed toward the treatment of pain and, in particular, to the therapeutic use of compounds that selectively reduce persistent sodium currents to treat chronic pain.

2. Background Information

The lipid bilayer membrane of all cells forms a barrier that is largely impermeable to the flux of ions and water. Residing within the membrane are a superfamily of proteins called ion channels, which provide selective pathways for ion flux. Precisely regulated conductances produced by ion channels are required for intercellular signaling and neuronal excitability. In particular, a group of ion channels that open upon depolarization of excitable cells are classified as voltage-gated and are responsible for electrical activity in nerve, muscle and cardiac tissue. In neurons, ion currents flowing through voltage-gated sodium channels are responsible for rapid spike-like action potentials. During action potentials the majority of sodium channels open very briefly. These brief openings result in transient sodium currents. However, a subset of voltage-gated sodium channels does not close rapidly, but remain open for relatively long intervals. These channels therefore generate sustained or persistent sodium currents. The balance between transient and persistent sodium current is crucial for maintaining normal physiological function and electrical signaling throughout the entire nervous system.

Clinical pain encompasses nociceptive and neuropathic pain. Each type of pain is characterized by hypersensitivity at the site of damage and in adjacent normal tissue. While nociceptive pain usually is limited in duration and responds well to available opioid therapy, neuropathic pain can persist long after the initiating event has healed, as is evident, for example, in phantom pain that often follows amputation. Chronic pain syndromes such as neuropathic pain can be triggered by a variety of causes, including, without limitation, a traumatic insult, such as, e.g., a compression injury, a spinal cord injury, a limb amputation, an inflammation or a surgical procedure; an ischemic event, such as, e.g., a stroke; an infectious agent; a toxin exposure, such as, e.g., a drug or alcohol; or a disease such as, e.g., an inflammatory disorder, a neoplastic tumor, acquired immune deficiency syndrome (AIDS) or a metabolic disease.

Unfortunately, chronic pain such as chronic neuropathic pain is generally resistant to available opioid and nonsteroidal antiinflammatory drug therapies. Available drug treatments for chronic neuropathic pain, such as tricyclic antidepressants; anti-convulsants/anti-epileptic, such as, e.g., carbamazepine, phenyloin and lamotrigine; and local anesthetics/antiarrythmics, such as, e.g., lidocaine, mexiletine, tocainide and flecainide, only temporarily alleviate symptoms and to varying degrees. In addition, current therapies have serious side effects that can include cognitive changes, sedation, nausea, emesis, dizziness, ataxia, tinnitus and, in the case of narcotic drugs, addiction. Further, many patients suffering from neuropathic and other chronic pain are elderly or have medical conditions that limit their tolerance to the side effects associated with available analgesic therapy, such as, e.g., cardiotoxicity, hepatic dysfunction and leukopenia. The inadequacy of current therapy in relieving chronic pain without producing intolerable side effects is reflected in the high rate of depression and suicide in chronic pain sufferers.

Recent evidence suggests that increased persistent sodium current may be an underlying basis for chronic pain, such as, e.g., inflammatory and neuropathic pain, see e.g., Fernando Cervero & Jennifer M. A. Laird, *Role of Ion Channels in Mechanisms Controlling Gastrointestinal Pain Pathways*, 3(6) CURR. OPIN. PHARMACOL. 608-612 (2003); Joel A. Black et al., *Changes in the Expression of Tetrodotoxin-Sensitive Sodium Channels Within Dorsal Root Ganglia Neurons in Inflammatory Pain*, 108(3) PAIN 237-247 (2004) and Li Yunru et al., *Role of Persistent Sodium and Calcium Currents in Motoneuron Firing and Spasticity in Chronic Spinal Rats*, 91(2) J. NEUROPHYSIOL. 767-783 (2004), which are hereby incorporated by reference in their entirety. However, at present, treatments for chronic pain characterized by aberrant levels of sodium channel current, such as, e.g., Berger et al., *Treatment of Neuropathic Pain*, U.S. Pat. No. 5,688,830 (Nov. 18, 1997); Marquess et al., *Sodium Channel Drugs and Uses*, U.S. Pat. No. 6,479,498 (Nov. 12, 2002); Choi et al., *Sodium Channel Modulators*, U.S. Pat. No. 6,646,012 (Nov. 11, 2003); and Chinn et al., *Sodium Channel Modulators*, U.S. Pat. No. 6,756,400 (Jun. 29, 2004), encompass general sodium channel modulators that effect transient currents. As such, the usefulness of available sodium channel blocking drugs is severely limited by potentially adverse side effects, such as, e.g., paralysis and cardiac arrest. Thus, there is a need for novel methods of treating chronic pain that directly modulate persistent sodium current. The present invention satisfies this need and provides related advantages as well.

SUMMARY OF THE INVENTION

The present invention provides methods of treating chronic pain in a mammal, including a human. In one embodiment, the method involves administering to the mammal an effective amount of a selective persistent sodium current antagonist that has at least 20-fold selectivity for a persistent sodium current relative to transient sodium current. In further embodiments, the antagonist has at least 50-fold selectivity for a persistent sodium current, at least 200-fold selectivity for a persistent sodium current, at least 400-fold selectivity for a persistent sodium current, at least 600-fold selectively for a persistent sodium current, or at least 1000-fold selectively for a persistent sodium current, relative to a transient sodium current. A variety of mammals can be treated by the methods of the invention including, without limitation, humans.

The present invention provides methods of treating a variety of types of chronic pain. In certain embodiments, the methods are directed to treating neuropathic pain, inflammatory pain such as arthritic pain, visceral pain, post-operative pain, pain resulting from cancer or cancer treatment, headache pain, irritable bowel syndrome pain, fibromyalgia pain, and pain resulting from diabetic neuropathy.

A variety of selective persistent sodium current antagonists can be useful in the methods of the invention. In one embodiment, a method of the invention is practiced by administering an effective amount of a selective $Na_v1.3$ antagonist that has at least 20-fold selectivity for $Na_v1.3$ persistent sodium current relative to transient sodium current. In further embodiments, the antagonist has at least 50-fold selectivity for the $Na_v1.3$ persistent sodium current; at least 200-fold selectivity for the $Na_v1.3$ persistent sodium current; at least 400-fold selectivity for the $Na_v1.3$ persistent sodium current; at least 600-fold selectively for the $Na_v1.3$ persistent sodium current; or at least 1000-fold selectively for the $Na_v1.3$ persistent sodium current, relative to transient sodium current.

In further embodiments, the methods of the invention involve administering an effective amount of a selective persistent sodium current antagonist belonging to one of the disclosed structural classes of selective persistent sodium current antagonists. Such a selective persistent sodium channel antagonist can be, without limitation, a compound represented by a formula selected from Formula 1:

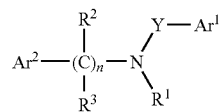

wherein,
$Ar^1$ is an aryl group;
$Ar^2$ is an aryl group;
Y is absent or is selected from:

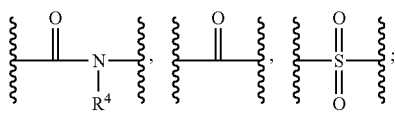

$R^1$ is selected from hydrogen, $C_1$-$C_8$ alkyl, aryl, arylalkyl;
$R^2$ and $R^3$ are independently selected from hydrogen, $C_1$-$C_8$ alkyl, aryl, arylalkyl, hydroxy, fluoro, $C_1$-$C_8$ carbocyclic ring, or $C_1$-$C_8$ heterocyclic ring;
$R^4$ is selected from hydrogen, $C_1$-$C_8$ alkyl, aryl, arylalkyl;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl; and
n is an integer of from 1 to 6;

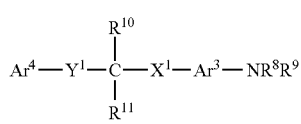

wherein,
$Ar^3$ is an aryl group;
$Ar^4$ is an aryl group;
$X^1$ and $Y^1$ are independently selected from

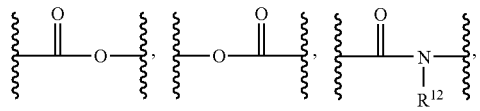

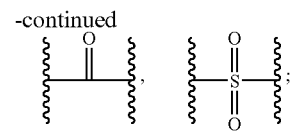

$R^5$ and $R^6$ are independently selected from hydrogen, fluoro, $C_1$ to $C_8$ alkyl, hydroxy;
$R^7$ is selected from hydrogen, $C_1$ to $C_8$ alkyl, aryl, arylalkyl;
$R^8$ and $R^9$ are selected from hydrogen, $C_1$-$C_8$ alkyl, aryl, arylalkyl, $COR^{12}$, $COCF_3$;
$R^{10}$ and $R^{11}$ are selected from hydrogen, halogen, hydroxyl, $C_1$-$C_8$ alkyl, aryl, arylalkyl, and
$R^{12}$ is selected from hydrogen, $C_1$-$C_8$ alkyl, aryl, arylalkyl;

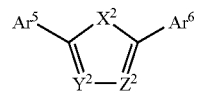

Formula 3 wherein,
$Ar^5$ is an aryl group;
$Ar^6$ is an aryl group;
$X^2$ is O, S, or $NR^{14}$;
$Y^2$ is N or $CR^{15}$;
$Z^2$ is N or $CR^{16}$;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl;
$R^{13}$ is selected from halogen, $C_1$-$C_8$ alkyl, arylalkyl, and $(CR^5R^6)_cN(R^7)_2$;
$R^{14}$ is selected from hydrogen, halogen, $C_1$ to $C_8$ alkyl, $CF_3$, $OCH_3$, $NO_2$, $(CR^5R^6)_cN(R^7)_2$;
$R^{15}$ is selected from hydrogen, halogen, $C_1$ to $C_8$ alkyl, $CF_3$, $OCH_3$, $NO_2$, $(CR^5R^6)_cN(R^7)_2$;
$R^{16}$ is selected from hydrogen, halogen, $C_1$ to $C_8$ alkyl, $CF_3$, $OCH_3$, $NO_2$, $(CR^5R^6)_cN(R^7)_2$; and
c is 0 or an integer from 1 to 5; and

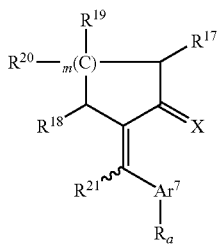

Formula 4 wherein,
$Ar^7$ is an aryl group;
R is selected from halogen, $C_1$-$C_8$ alkyl, $NR^{22}R^{23}$, $OR^{22}$;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl;
$R^{17}$ and $R^{13}$ are independently selected hydrogen, $C_1$-$C_8$ alkyl, aryl, arylalkyl, hydroxy;

$R^{19}$ and $R^{20}$ are independently selected from hydrogen, halogen, $C_1$-$C_8$ alkyl, hydroxy, amino, $CF_3$;

$R^{21}$, $R^{22}$, and $R^{23}$ are independently selected from hydrogen, aryl or $C_1$-$C_8$ alkyl;

a is 0 or an integer from 1 to 5; and m is 0 or and integer from 1 to 3.

A compound corresponding to any of the above formulas also can be a pharmaceutically acceptable salt, ester, amide, or geometric, steroisomer, or racemic mixture.

Any of the variety of routes of administration can be useful for treating chemical pain according to a method of the invention. In particular embodiments, administration is performed peripherally, systemically or orally.

BRIEF DESCRIPTION OF THE DRAWINGS

FIG. 1 shows four compounds that are selective persistent sodium current antagonists.

DETAILED DESCRIPTION OF THE INVENTION

I. Voltage-Gated Sodium Channels

Figure 2:
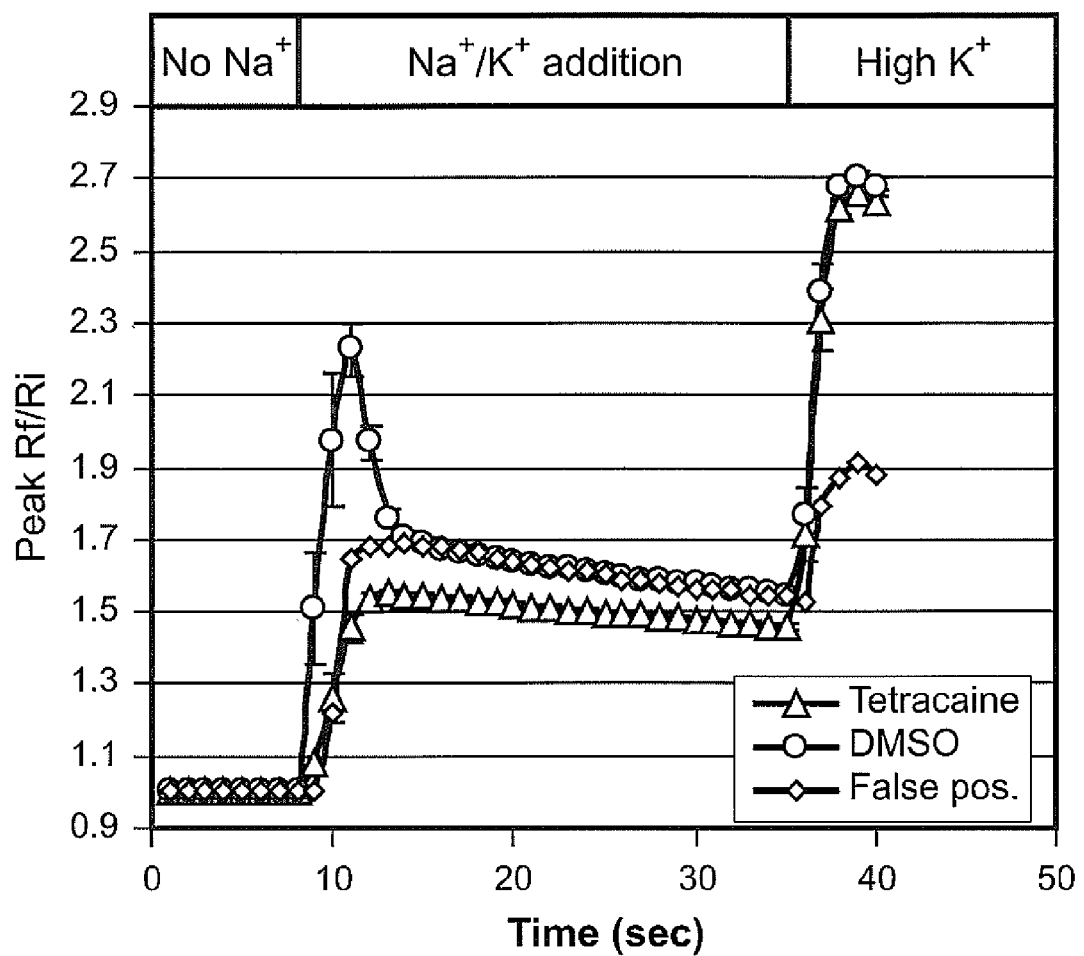
FIG. 2 shows inhibition of persistent current-dependent depolarization by sodium channel blockers. In the this assay, cells are resting in wells containing 80 µl of TEA-MeSO$_3$ (sodium-free box) to which is added 240 µl of NaMeSO$_3$ buffer containing 13 mM KMeSO$_3$ for a final K$^+$ concentration of 10 mM and a final Na$^+$ concentration of 110 mM (sodium/potassium-addition). This elicits a robust depolarizing response. Following the resolution of the sodium-dependent depolarization, a second aliquot of KMeSO$_3$ is added to the well bringing the final K$^+$ concentration to 80 mM (High potassium-addition). This addition results in a second depolarizing response. Compounds that reduce the sodium-dependent, but not the potassium-dependent depolarizations are selected as persistent sodium channel blockers. Circles indicate the control response with 0.1% DMSO added, triangles show the effects of the sodium channel inhibitor tetracaine (10 µM) and the diamonds show the response during the application of a non-specific channel blocker.

In the normal functioning of the nervous system, neurons are capable of receiving a stimulus, and in response, propagating an electrical signal away from their neuron cell bodies (soma) along processes (axons). From the axon, the signal is delivered to the synaptic terminal, where it is transferred to an adjacent neuron or other cell. Voltage-sensitive sodium channels have an important role in nervous system function because they mediate propagation of electrical signals along axons.

Voltage-gated sodium channels are members of a large mammalian gene family encoding at least 9 alpha- and 3 beta-subunits. While all members of this family conduct Na$^+$ ions through the cell membrane, they differ in tissue localization, regulation and, at least in part, in kinetics of activation and inactivation, see, e.g., William A. Catterall, *From Ionic Currents to Molecular Mechanism: The Structure and Function of Voltage-gated Sodium Channels*, 26(1) NEURON 13-25 (2000); and Sanja D. Novakovic et al., *Regulation of Na$^+$ Channel Distribution in the Nervous System*, 24(8) TRENDS NEUROSCI. 473-478 (2001), which are hereby incorporated by reference in their entirety.

Generally, under resting conditions, sodium channels are closed until a stimulus depolarizes the cell to a threshold level. At this threshold, sodium channels begin to open and then rapidly generate the upstroke of the action potential. Normally during an action potential, sodium channels open briefly (one millisecond) and then close (inactivate) until the excitable cell returns to its resting potential and the sodium channels re-enter the resting state.

Without wishing to be bound by the following, this behavior of voltage-gated sodium channels can be understood as follows. Sodium channels can reside in three major conformations or states. The resting or "closed" state predominates at negative membrane potentials ($\leq$–60 mV). Upon depolarization, channels open and allow current to flow. Transition from the resting state to the open state occurs within a millisecond after depolarization to positive membrane potentials. Finally, during sustained depolarization (>1-2 ms), channels enter a second closed or inactive state. Subsequent re-opening of channels requires recycling of channels from an inactive state to a resting state, which occurs when the membrane potential returns to a negative value (repolarization). Therefore, membrane depolarization not only causes sodium channels to open, but also causes them to close, during sustained depolarization.

A small fraction of the sodium channels can fail to inactivate even with sustained depolarization. This non-inactivating sodium current is called a "persistent" sodium current. Four sodium channels, Nav1.3, Nav1.5, Nav1.6 and Nav1.9, have historically been known to generate a persistent current. Recent evidence, however, suggests that all voltage-gated sodium channels are capable of producing a persistent current, see, e.g., Abraha Taddese & Bruce P. Bean, *Subthreshold*

Sodium Current from Rapidly Inactivating Sodium Channels Drives Spontaneous Firing of Tubermammillary Neurons, 33(4) NEURON 587-600 (2002); Michael Tri H. Do & Bruce P. Bean, *Subthreshold Sodium Currents and Pacemaking of Subthalamic Neurons: Modulation by Slow Inactivation,* 39(1) NEURON 109-120 (2003), which are hereby incorporated by reference in their entirety. The mechanism that produces a persistent current is poorly understood. Two hypothesis are (1) that different sodium channels produce transient and persistent currents, and (2) that a sodium channel capable of producing transient sodium current enters a different gating mode to produce a persistent current. Persistent sodium channels can open at more negative membrane potentials relative to normal sodium channels and inactivate at more positive potentials, see, e.g., Jacopo Magistretti & Angel Alonso, *Biophysical Properties and Slow-voltage Dependent Inactivation of a Sustained Sodium Current in Entorhinal Cortex Layer-II Principal Neurons: A Whole-Cell and Single-Channel Study* 114(4) J. GEN. PHYSIOL. 491-509 (1999). Persistent sodium current have been observed at membrane potentials as negative as −80 mV, see, e.g., Peter K. Stys, *Anoxic and Ischemic Injury of Myelinated Axons in CNS White Matter: From Mechanistic Concepts to Therapeutics,* 18(1) J. CEREB. BLOOD FLOW METAB. 2-25 (1998) and have been shown to persist for seconds following depolarization at potentials as positive as 0 mV, see, e.g., Magistretti & Alonso, supra, (1999). Thus, persistent sodium current is distinct from, and can be readily distinguished from, transient sodium current.

Although the physiological role of persistent sodium current is not fully understood, such current can function in generating rhythmic oscillations; integrating synaptic input; modulating the firing pattern of neurons; and regulating neuronal excitability and firing frequency, see, e.g., Wayne E. Crill, *Persistent Sodium Current in Mammalian Central Neurons* 58 ANNU. REV. PHYSIOL. 349-362 (1996); and David S. Ragsdale & Massimo Avoli, *Sodium Channels as Molecular Targets for Antiepileptic Drugs,* 26(1) BRAIN RES. BRAIN RES. REV. 16-28 (1998). Persistent sodium current also can induce deleterious phenomena, including cardiac arrhythmia, epileptic seizure, and neuronal cell death under ischemic and anoxic conditions, see, e.g., Christoph Lossin et al., *Molecular Basis of an Inherited Epilepsy* 34(6) NEURON 877-84 (2002); Peter K. Stys et al., *Ionic Mechanisms of Anoxic Injury in Mammalian CNS White Matter: Role of $Na^+$ Channels and $Na(+)$-$Ca2+$ Exchanger,* 12(2) J. NEUROSCI. 430-439 (1992); Peter K. Stys et al., *Noninactivating, Tetrodotoxin-Sensitive $Na^+$ Conductance in Rat Optic Nerve Axons,* 90(15) PROC. NATL. ACAD. SCI. USA, 6976-6980 (1993); and Giti Garthwaite et al., *Mechanisms of Ischaemic Damage to Central White Matter Axons: A Quantitative Histological Analysis Using Rat Optic Nerve,* 94(4) NEUROSCIENCE 1219-1230 (1999). Thus, aberrant persistent sodium current can contribute to development or progression of pathological conditions by collapsing the normal cell transmembrane gradient for sodium, leading to reverse operation of the sodium-calcium exchanger, and resulting in an influx of intracellular calcium, which injures the axon, see, e.g., Stys et al., supra, (1992).

While abnormal activity of a persistent current can underlie a wide array of chronic pain conditions, the underlying mechanisms appears to be similar. It is generally understood that abnormally increased persistent sodium current can depolarize the resting membrane potential or reduce the rate of repolarization during an action potential. Either effect may produce a state of hyper-excitability in which aberrant neuronal behavior is manifested. This aberrant neuronal behavior can result in a neuron with increased firing rates, enhanced sensitivity to synaptic input or abnormal repetitive or rhythmic firing patterns. It is also generally understood that abnormally high levels of persistent current generate sustained membrane depolarization and a concomitant increase of $Na^+$ within the cell. This high $Na^+$ influx, in turn, drives the sodium/calcium exchanger, which in turn, results in detrimental levels of $Ca^{2+}$ to accumulate inside affected cells. Abnormally high levels of $Ca^{2+}$ result in neuronal cell dysfunction and neuronal cell death. Thus, by collapsing the normal cell transmembrane gradient for sodium, a persistent current can reverse the operation of the sodium-calcium exchanger, and the resulting an influx of intracellular calcium would cause injuries or death to a nerve. As disclosed herein, conditions associated with aberrant persistent sodium current can be treated by selectively inhibiting or reducing persistent sodium current without compromising normal transient sodium current function, thereby allowing normal neuronal function (excitability). As disclosed herein, pain conditions associated with aberrant persistent sodium current can be treated by selectively inhibiting or reducing persistent sodium current without compromising normal transient sodium current function.

II. Chronic Pain and Persistent Sodium Current

There is strong evidence that altered voltage-gated sodium channel activity plays a critical role in chronic pain, such as, e.g., inflammatory and neuropathic pain, see, e.g., Mark D. Baker & John N. Wood, *Involvement of $Na^+$ Channels in Pain Pathways,* 22(1) TRENDS PHARMACOL. SCI. 27-31 (2001); John N. Wood et al., *Sodium Channels in Primary Sensory Neurons: Relationship to Pain States,* 241 NOVARTIS FOUND. SYMP. 159-168 (2002); Josephine Lai et al., *The Role of Voltage-gated Sodium Channels in Neuropathic Pain,* 13(3) CURR. OPIN. NEUROBIOL. 291-297 (2003); Philip LoGrasso & Jeffrey McKelvy, *Advances in Pain Therapeutics,* 7(4) Curr. Opin. Chem. Biol. 452-456 (2003); Phillip J. Birch et al., *Strategies to Identify Ion Channel Modulators: Current and Novel Approaches to Target Neuropathic Pain,* 9(9) DRUG DISCOV. TODAY 410-418 (2004); and Josephine Lai et al., *Voltage-gated sodium channels and hyperalgesia,* 44 ANNU. REV. PHARMACOL. TOXICOL. 371-397 (2004), which are hereby incorporated by reference in their entirety. Alterations in sodium channel expression and/or function has a profound effect on the firing pattern of neurons in both the peripheral and central nervous systems. For example, injury to sensory primary afferent neurons often results in rapid redistribution of voltage-gated sodium channels along the axon and dendrites and in abnormal, repetitive discharges or exaggerated responses to subsequent sensory stimuli. Such an exaggerated response is considered to be crucial for the incidence of spontaneous pain in the absence of external stimuli that is characteristic of chronic pain. In addition, inflammatory pain is associated with lowered thresholds of activation of nociceptors in the periphery and altered sodium channel function is thought to underlie aspects of this phenomenon. Likewise, neuropathic pain states resulting from peripheral nerve damage is associated with altered sodium channel activity and ectopic action potential propagation.

Importantly, sodium channel inhibitors are clinically effective in the treatment of many types of chronic pain. For example, local anesthetics (such as, e.g., lidocaine, mexiletine, tocainide and flecainide) have been reported to provide effective relief in painful diabetic neuropathy, neuralgic pain, lumbar radiculopathies, complex regional pain syndrome Type I and Type II and traumatic peripheral injuries. Anticonvulsants (such as, e.g., carbamazepine and phenyloin) used as analgesics to treat chronic pain associated with neuralgic pain, trigeminal neuralgia, diabetic neuropathy. Anti-epileptic agents (such as, e.g., lamotrigine) are used with trigeminal neuralgia, diabetic neuropathy, postherpetic neuralgia, complex regional pain syndrome Type II and phantom pain. However, the usefulness of available sodium channel blocking drugs is severely limited by their failure to discriminate adequately between sodium channel a subunits. Highly systemic concentration would be associated with devastating side-effects, such as, e.g., periodic paralyses in muscle, cardiac arrest due to ventricular fibrillation and delayed cardiac repolarization in the heart, and epilepsy in the central nervous system, see, e.g., Baker & Wood, supra, (2001); and Lai et al., supra, (2004).

Recent evidence has revealed that increased activity from a persistent sodium current may be responsible for the underlying basis of chronic pain, see e.g., Cervero & Laird, supra, (2003); Black et al., supra, (2004); and Yunru et al., supra, (2004), which are hereby incorporated by reference in their entirety. An example of a sodium channel capable of mediating persistent current is the type III sodium channel $Na_v1.3$. Under pathological pain circumstances, $Na_v1.3$ expression can become upregulated while other sodium channels are concomitantly downregulated. For example, in adult rodents, damage to sensory neurons results in upregulation of $Na_v1.3$ and downregulation of $Na_v1.8$ and $Na_v1.9$, see, e.g., Birch et al., supra, (2004), which is hereby incorporated by reference in its entirety. Furthermore, this $Na_v1.3$ upregulation after nerve injury is associated with increased membrane potential oscillations that appear to underlie spontaneous activity, see, e.g., Bryan C. Hains et al., *Upregulation of Sodium Channel $Na_v1.3$ and Functional Involvement in Neuronal Hyperexcitability Associated With Central Neuropathic Pain After Spinal Cord Injury,* 23(26) J. NEUROSCI. 8881-8892 (2003); and Bryan C. Hains et al., *Altered Sodium Channel Expression in Second-Order Spinal Sensory Neurons Contributes to Pain after Peripheral Nerve Injury,* 24(20) J. NEUROSCI. 4832-4839 (2004), which are hereby incorporated by reference in their entirety. Selective reduction in the expression or activity of sodium channels capable of mediating persistent current relative to any reduction in normal voltage-gated (transient) sodium current can be useful for treating conditions associated with increased persistent sodium current.

Therefore, chronic pain is an example of a condition associated with increased persistent sodium current. As described herein, a compound that decreases persistent sodium current without a similar decrease in normal transient sodium current can effectively treat chronic pain without harmful side effects that generally accompany non-selective sodium channel blockers. As disclosed in Example 4, a selective persistent sodium current antagonist can effectively reverse allodynia in an animal model of neuropathic pain. Therefore, based on the identification of selective persistent sodium channel antagonists that have at least 20-fold selectivity for persistent sodium channel relative to transient sodium current, and the demonstration of the effectiveness of treating pain by selectively antagonizing persistent sodium current, the present invention provides a method of treating chronic pain in a mammal by selectively antagonizing persistent sodium current. The method involves administering to the mammal an effective amount of a selective persistent sodium channel antagonist that has at least 20-fold selectivity for persistent sodium current relative to transient sodium current.

The methods of the invention are useful for treating any of a variety of types of chronic pain, and, as non-limiting examples, pain that is neuropathic, visceral or inflammatory in origin. In particular embodiments, the methods of the invention are used to treat neuropathic pain; visceral pain; post-operative pain; pain resulting from cancer or cancer treatment; fibromyalgia pain, and inflammatory pain.

As used herein, the term "pain" encompasses both acute and chronic pain. As used herein, the term "acute pain" means immediate, generally high threshold, pain brought about by injury such as a cut, crush, burn, or by chemical stimulation such as that experienced upon exposure to capsaicin, the active ingredient in chili peppers. The term "chronic pain," as used herein, means pain other than acute pain and includes, without limitation, neuropathic pain, visceral pain, inflammatory pain, headache pain, muscle pain and referred pain. It is understood that chronic pain often is of relatively long duration, for example, months or years and can be continuous or intermittent.

In one embodiment, the methods of the invention are used to treat "neuropathic pain," which, as used herein, means abnormal sensory input by either the peripheral nervous system, central nervous systems, or both resulting in discomfort. Neuropathic pain typically is long-lasting or chronic and can develop days or months following an initial acute tissue injury. Symptoms of neuropathic pain can involve persistent, spontaneous pain, as well as allodynia, which is a painful response to a stimulus that normally is not painful, hyperalgesia, an accentuated response to a painful stimulus that usually a mild discomfort, such as a pin prick, or hyperpathia, a short discomfort becomes a prolonged severe pain. Neuropathic pain generally is resistant to opioid therapy. Neuropathic pain can be distinguished from nociceptive pain, which is pain caused by the normal processing of stimuli resulting from acute tissue injury. In contrast to neuropathic pain, nociceptive pain usually is limited in duration to the period of tissue repair and usually can be alleviated by available opioid and non-opioid analgesics.

The methods of the invention are useful for treating both centrally-generated and peripherially-generated neuropathic pain resulting from, without limitation, a trauma or disease of peripheral nerve, dorsal root ganglia, spinal cord, brainstem, thalamus or cortex. Examples of neuropathic pain that can be treated by the methods of the invention include neuralgia, such as, e.g., trigeminal neuralgia, post-herpetic neuralgia, glossopharyngeal neuralgia, sciatica and atypical facial pain; deafferentation pain syndromes, such as, e.g., injury to the brain or spinal cord, post-stroke pain, phantom pain, paraplegia, peripheral nerve injuries, brachial plexus avulsion injuries, lumbar radiculopathies and postherpetic neuralgia; complex regional pain syndromes (CRPSs) such as, e.g., reflex sympathetic dystrophy (CRPS Type I) and causalgia (CRPS Type II); and polyneuropathic pain, such as, e.g., diabetic neuropathy, chemotherapy-induced pain, treatment-induced pain, and postmastectomy syndrome. It is understood that the methods of the invention are useful in treating neuropathic pain regardless of the etiology of the pain. As non-limiting examples, the methods of the invention can be used to treat neuropathic pain resulting from a peripheral nerve disorder such as neuroma; from nerve compression; from nerve crush or stretch, nerve entrapment or incomplete nerve transsection; or from a mononeuropathy or a polyneuropathy. As further non-limiting examples, the methods of the invention are useful in treating neuropathic pain resulting from a disorder such as dorsal root ganglion compression; inflammation of the spinal cord; contusion, tumor or hemisection of the spinal cord; and tumors or trauma of the brainstem, thalamus or cortex.

As indicated above, the methods of the invention can be useful for treating neuropathic pain resulting from a mononeuropathy, polyneuropathy, complex regional pain syndromes or deafferentation. A neuropathy is a functional disturbance or pathological change in the peripheral nervous system and is characterized clinically by sensory or motor neuron abnormalities. The term mononeuropathy indicates that a single peripheral nerve is affected, while the term polyneuropathy indicates that several peripheral nerves are affected. Deafferentation indicates a loss of the sensory input from a portion of the body, and can be caused by interruption of either peripheral sensory fibres or nerves from the central nervous system. The etiology of a neuropathy can be known or unknown. Known etiologies include complications of a disease or toxic state such as diabetes, which is the most common metabolic disorder causing neuropathy, or irradiation, ischemia or vasculitis. Polyneuropathies that can be treated by a method of the invention can result, without limitation, from post-polio syndrome, diabetic neuropathy, alcohol neuropathy, amyloid, toxins, AIDS, hypothyroidism, uremia, vitamin deficiencies, chemotherapy, 2',3'-didexoycytidine (ddC) treatment, Guillain-Barré syndrome or Fabry's disease. It is understood that the methods of the invention can be used to treat chronic pain of these or other chronic neuropathies of known or unknown etiology.

The methods of the invention also can used for treating chronic pain resulting from excessive muscle or nerve tension, such as certain types of back pain, such as that resulting from a herniated disc; a bone spur, sciatica, sprains, strains and joint pain. The methods of the invention can further be used for treating chronic pain resulting from activity, such as, as non-limiting examples, long hours of work at a computer, work with heavy objects or heavy machinery, or spending long hours on one's feet, and repetitive motion disorders (RMDs). RMDs are a variety of muscular conditions that can cause chronic pain. RMDs can be caused by overexertion, incorrect posture, muscle fatigue, compression of nerves or tissue, too many uninterrupted repetitions of an activity or motion, or friction caused by an unnatural or awkward motion such as twisting the arm or wrist. Common RMDs occur in the hands, wrists, elbows, shoulders, neck, back, hips, knees, feet, legs, and ankles, however, the hands and arms are most often affected. The methods of the invention can be used to treat chronic pain arising from any type of RMD. The methods of the invention further can be used to treat chronic muscle pain, chronic pain associated with substance abuse or withdrawal, and other types of chronic pain of known or unknown etiology.

Similarly, the methods of the invention can be used to treat chronic pain resulting from an inflammatory disorder, for example, from arthritis/connective tissue disorders such as, e.g., osteoarthritis, rheumatoid arthritis, juvenile arthritis, gouty arthritis; spondyloarthritis, scleroderma and fibromyalgia; autoimmune diseases such as, e.g., Guillain-Barré syndrome, myasthenia gravis and lupus erythematosus; inflammation caused by injury, such as a crush, puncture, stretch of a tissue or joint; inflammation caused by infection, such as tuberculosis; or neurogenic inflammation.

The methods of the invention can also be used to treat visceral pain, such as, e.g., functional visceral pain including chronic gastrointestinal inflammations like Crohn's disease, ulcerative colitis, gastritis, irritable bowel syndrome; orangic visceral pain including pain resulting from a traumatic, inflammatory or degenerative lesion of the gut or produced by a tumor impinging on sensory innervation; and treatment-induced visceral pain, for example, attendant to chemotherapy or radiation therapy.

The methods of the invention can be used for treating chronic pain resulting from headache, including, without limitation, tension-type headache, migraine headache, cluster headache, hormone headache, rebound headache, sinus headache, and organic headache. The methods of the invention can be used for treating chronic pain resulting infections, such as, e.g., Lymes disease, HIV/AIDS and leprosy.

III. Selective Persistent Sodium Current Blockers

The methods of the invention involve administering a compound that selectively reduces persistent sodium current relative to transient sodium current. As used herein, the term "selective," when used herein in reference to a compound, such as an antagonist, means a compound that, at least one particular dose reduces persistent sodium current at least 20-fold more than transient sodium current is reduced. Therefore, a compound that selectively reduces persistent sodium current has at least 20-fold selectively for persistent sodium current relative to transient sodium current, and can have, for example, at least 50-fold selectively for persistent sodium current relative to transient sodium current, at least 100-fold, at least 200-fold, at least 400-fold, at least 600-fold, or at least 1000-fold selectively for persistent sodium current relative to transient sodium current.

As used herein, the term "persistent sodium current" means a sodium channel mediated current that is non-transient; that can remain active during prolonged depolarization or that activates at voltage more negative than −60 mV and thus can contribute to hyperexcitability of the neural membrane. Prolonged depolarization refers to depolarization that occurs over a time period greater than the time period during which a transient current typically inactivates. As a non-limiting example, prolonged depolarization can occur within a time period greater than the time period during which the transient current of a sodium channel, such as $Na_v1.2$, typically inactivates. Therefore, prolonged depolarization refers to depolarization that persists for at least 0.002 second, such as at least 0.01 second, at least 0.1 second and at least 1 second.

A compound that selectively reduces persistent sodium current can be, for example, a persistent sodium channel antagonist. As used herein, the term "persistent sodium channel antagonist," means a compound that inhibits or decreases persistent current mediated through a sodium channel by binding to the sodium channel. It is understood that a persistent sodium channel antagonist can act by any antagonistic mechanism, such as by directly binding a persistent sodium channel at the pore entrance, thereby inhibiting movement of ions through the channel, or by binding a channel at another site to alter channel conformation and inhibit movement of ions through the channel. Exemplary selective persistent sodium channel antagonists that represent four structural classes of organic molecules are disclosed herein as Formulas 1, 2, 3 and 4.

It further is understood that a compound that selectively reduces persistent sodium current can act indirectly, for example, by reducing or down-regulating expression of a persistent sodium channel, for example, by inactivating a positive regulator of transcription or activating a negative regulator of transcription, without a corresponding reduction transient sodium channel; by increasing the expression or activity of a molecule that inactivates or reduces persistent sodium channel function, such as a protease, modifying enzyme or other molecule, without a corresponding reduction in transient sodium current; or by decreasing the expression or activity of a molecule that transmits a downstream signal from a persistent sodium current without a corresponding reduction in transient sodium current, for example, without substantially altering the downstream signal from a transient sodium channel.

As disclosed herein, structurally unrelated molecules can have at least 20-fold selectivity for reducing persistent sodium current relative to transient sodium current and, therefore, can be useful in the methods of the invention. For example, such a compound can be a naturally or non-naturally occurring macromolecule, such as a peptide, peptidomimetic, nucleic acid, carbohydrate or lipid. The compound further can be an antibody, or antigen-binding fragment thereof such as a monoclonal antibody, humanized antibody, chimeric antibody, minibody, bifunctional antibody, single chain antibody (scFv), variable region fragment (Fv or Fd), Fab or F(ab)₂. The compound also can be a partially or completely synthetic derivative, analog or mimetic of a naturally occurring macromolecule, or a small organic or inorganic molecule.

A selective persistent sodium current antagonist that is a nucleic acid can be, for example, an anti-sense nucleotide sequence, an RNA molecule, or an aptamer sequence. An anti-sense nucleotide sequence can bind to a nucleotide sequence within a cell and modulate the level of expression of a persistent sodium channel gene, or modulate expression of another gene that controls the expression or activity of a persistent sodium channel. Similarly, an RNA molecule, such as a catalytic ribozyme, can bind to and alter the expression of a persistent sodium channel gene, or other gene that controls the expression or activity of a persistent sodium channel. An aptamer is a nucleic acid sequence that has a three dimensional structure capable of binding to a molecular target, see, e.g., Sumedha D. Jayasena, *Aptamers: An Emerging Class of Molecules That Rival Antibodies in Diagnostics*, 45(9) CLIN. CHEM. 1628-1650 (1999), which is hereby incorporated by reference in its entirety. As such, an aptamer can serve as a persistent sodium current selective compound.

A selective persistent sodium current antagonist that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Sayda M. Elbashir et al., *Duplexes of 21-nucleotide RNAs Mediate RNA Interference in Cultured Mammalian Cells*, 411(6836) NATURE 494-498 (2001); B. L. Bass, *RNA Interference. The Short Answer*, 411(6836) NATURE 428-429 (2001); Phillip D. Zamore, *RNA Interference: Listening to the Sound of Silence*, 8(9) NAT. STRUCT. BIOL. 746-750 (2001), which are hereby incorporated by reference in their entirety. dsRNAs of about 25-30 nucleotides have also been used successfully for RNAi (Anton Karabinos et al., *Essential Roles for Four Cytoplasmic Intermediate Filament Proteins in Caenorhabditis elegans Development*, 98(14) PROC. NATL. ACAD. SCI. USA 7863-7868 (2001), which is hereby incorporated by reference in its entirety. dsRNA can be synthesized in vitro and introduced into a cell by methods known in the art.

A persistent sodium channel selective compound that is an antibody can be, for example, an antibody that binds to a persistent sodium channel and inhibits movement of ions through the channel, or alters the activity of a molecule that regulates persistent sodium current expression or activity, such that sodium current is decreased. It is understood that such a compound binds selectively such that a corresponding reduction in transient sodium current is not affected.

A persistent sodium channel selective compound that is a small molecule can have a variety of structures. In several embodiments, a compound that selectively reduces persistent sodium current that has at least 20-fold selectivity for reducing persistent sodium current to non-persistent sodium current is an organic molecule represented by a formula shown herein below, or a pharmaceutically acceptable salt, ester, amide, stereoisomer or racemic mixture thereof. As disclosed herein in FIG. 1, several identified compounds are selective for persistent sodium current relative to transient sodium current, with selectivities of 32-fold, 38-fold, 110-fold and 453-fold. It is understood that these and other compounds with at least 20-fold selectivity for persistent sodium current relative to transient sodium current, for example, identified by the methods disclosed herein in Examples 1, 2, 3 and 4 can be useful for treating chronic pain according to a method of the invention.

In one embodiment, a compound useful in a method of the invention, or a pharmaceutically acceptable salt, ester, amide, stereoisomer or racemic mixture thereof, has a structure from Formula 1:

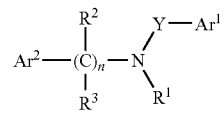

wherein, $Ar^1$ is an aryl group;

$Ar^2$ is an aryl group;

Y is absent or is selected from:

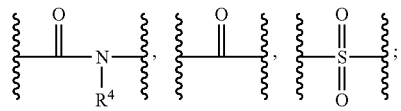

$R^1$ is selected from hydrogen, $C_1$-$C_8$ alkyl, aryl, or arylalkyl;

$R^2$ and $R^3$ are independently selected from hydrogen, $C_1$-$C_8$ alkyl, aryl, arylalkyl, hydroxy, fluoro, $C_1$-$C_8$ carbocyclic ring, or $C_1$-$C_8$ heterocyclic ring;

$R^4$ is selected from hydrogen, $C_1$-$C_8$ alkyl, aryl, or arylalkyl;

$R^5$ and $R^6$ are selected from hydrogen, fluoro, $C_1$ to $C_8$ alkyl, or hydroxy;

$R^7$ is selected from hydrogen, $C_1$ to $C_8$ alkyl, aryl, or arylalkyl, and n is an integer of from 1 to 6.

In one aspect of this embodiment, $Ar^1$ is thienyl, or substituted thienyl. For example, the thienyl can be substituted with one or more of halogen, $C_1$-$C_8$ alkyl, $NO_2$, $CF_3$, $OCF_3$, $OCF_2H$, CN, $(CR^5R^6)_cN(R^7)_2$, wherein c is 0 or an integer from 1 to 5; and In another aspect of this embodiment, $Ar^2$ is phenyl or substituted phenyl. For example, the phenyl can be substituted with halogen, $C_1$-$C_8$ alkyl, arylalkyl, $NO_2$, $CF_3$, $OCF_3$, $OCF_2H$, CN and $(CR^5R^6)_cN(R^7)_2$, wherein c is 0 or an integer from 1 to 5.

In another embodiment, a compound useful in a method of the invention, or a pharmaceutically acceptable salt, ester, amide, stereoisomer or racemic mixture thereof, has a structure from Formula 2:

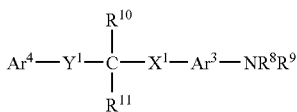

wherein,
$Ar^3$ is an aryl group;
$Ar^4$ is an aryl group;
$X^1$ and $Y^1$ are independently selected from:

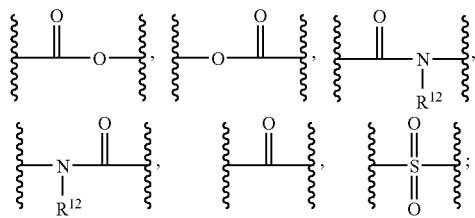

$R^5$ and $R^6$ are independently selected from: hydrogen, fluoro, $C_1$ to $C_8$ alkyl, hydroxy;
$R^7$ is selected from hydrogen, $C_1$ to $C_8$ alkyl, aryl, arylalkyl;
$R^8$ and $R^9$ are selected from hydrogen, $C_1$-$C_8$ alkyl, aryl, arylalkyl, $COR^{12}$, $COCF_3$;
$R^{10}$ and $R^{11}$ are selected from hydrogen, halogen, hydroxyl, $C_1$-$C_8$ alkyl, aryl, arylalkyl; and
$R^{12}$ is selected from hydrogen, $C_1$-$C_8$ alkyl, aryl, arylalkyl.

In one aspect of this embodiment, $Ar^3$ can be phenyl or substituted phenyl. For example, the phenyl can be substituted with one or more of halogen, $C_1$-$C_8$ alkyl, $NO_2$, $CF_3$, $OCF_3$, $OCF_2H$, CN, $(CR^5R^6)_cN(R^7)_2$, wherein c is 0 or an integer from 1 to 5.

In another aspect of this embodiment, $Ar^4$ is substituted with one or more of halogen, $C_1$-$C_8$ alkyl, arylalkyl, $NO_2$, $CF_3$, $OCF_3$, $OCF_2H$, CN or $(CR^5R^6)_cN(R^7)_2$, wherein c is 0 or an integer from 1 to 5.

In yet another embodiment, a compound useful in a method of the invention, or a pharmaceutically acceptable salt, ester, amide, stereoisomer or racemic mixture thereof, has a structure from Formula 3:

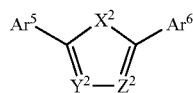

wherein,
$Ar^5$ is an aryl group;
$Ar^6$ is an aryl group;
$X^2$ is O, S, or $NR^{14}$;
$Y^2$ is N or $CR^{15}$;
$Z^2$ is N or $CR^{16}$;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl;
$R^{13}$ is selected from halogen, $C_1$-$C_8$ alkyl, arylalkyl, and $(CR^5R^6)_cN(R^7)_2$;
$R^{14}$ is selected from hydrogen, halogen, $C_1$ to $C_8$ alkyl, $CF_3$, $OCH_3$, $NO_2$, $(CR^5R^6)N(R^7)_2$;

$R^{15}$ is selected from hydrogen, halogen, $C_1$ to $C_8$ alkyl, $CF_3$, $OCH_3$, $NO_2$, $(CR^5R^6)N(R^7)_2$;
$R^{16}$ is selected from hydrogen, halogen, $C_1$ to $C_8$ alkyl, $CF_3$, $OCH_3$, $NO_2$, $(CR^5R^6)_cN(R^7)_2$, and
wherein c is 0 or an integer from 1 to 5.

In one aspect of this embodiment, $Ar^5$ is phenyl or substituted phenyl. For example, the phenyl can be substituted with one or more of halogen, $C_1$-$C_8$ alkyl, $NO_2$, $CF_3$, $OCF_3$, $OCF_2H$, CN, or $(CR^5R^6)_cN(R^7)_2$, wherein c is 0 or an integer from 1 to 5.

In another aspect of this embodiment, $Ar^6$ is substituted with halogen, $C_1$-$C_8$ alkyl, arylalkyl, $NO_2$, $CF_3$, $OCF_3$, $OCF_2H$, CN or $(CR^5R^6)_cN(R^7)_2$ wherein c is 0 or an integer from 1 to 5.

In yet another aspect of this embodiment, $Ar^6$ is selected from:

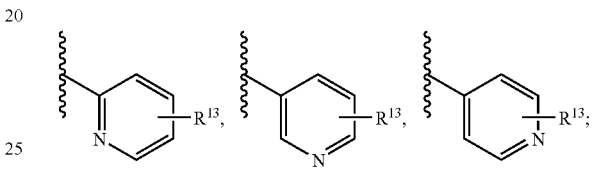

In yet another embodiment, a compound useful in a method of the invention, or a pharmaceutically acceptable salt, ester, amide, stereoisomer or racemic mixture thereof, has a structure from Formula 4:

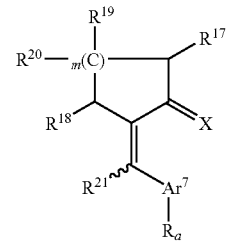

wherein,
$Ar^7$ is an aryl group;
$R_a$ is selected from halogen, $C_1$-$C_8$ alkyl, $NR^{22}R^{23}$, $OR^{22}$;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl;
$R^{17}$ and $R^1$ are independently selected hydrogen, $C_1$-$C_8$ alkyl, aryl, arylalkyl, and hydroxy;
$R^{19}$ and $R^{20}$ are independently selected from hydrogen, halogen, $C_1$-$C_8$ alkyl, hydroxy, amino, $CF_3$;
$R^{21}$, $R^{22}$, and $R^{23}$ are independently selected from hydrogen, aryl or $C_1$-$C_8$ alkyl;
a is 0 or an integer from 1 to 5, and
m is 0 or and integer from 1 to 3.

In one aspect of this embodiment, $Ar^7$ is phenyl or substituted phenyl. For example the phenyl can be substituted with one or more of halogen, $C_1$-$C_8$ alkyl, $NO_2$, $CF_3$, $OCF_3$, $OCF_2H$, CN, $(CR^5R^6)_cN(R^7)_2$, wherein c is 0 or an integer from 1 to 5.

In another aspect of this embodiment, R is amino or

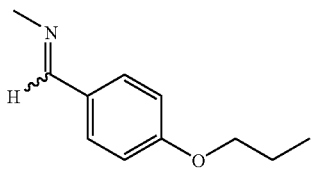

In yet another aspect of this embodiment, $R^{17}$ is isopropyl; in one embodiment, $R^{18}$ is methyl.

Exemplary compounds that are persistent sodium channel antagonists useful in a method of the invention are shown as Formulas 1, 2, 3 and 4. In addition, the compounds shown in FIG. 1 have selectivities for persistent sodium current of 32-fold, 38-fold, 110-fold, and 453-fold, relative to transient sodium current.

As used herein, the term "alkyl" means a straight-chain, branched or cyclic saturated aliphatic hydrocarbon. For example, an alkyl group can have 1 to 12 carbons, such as from 1 to 7 carbons, or from 1 to 4 carbons. Exemplary alkyl groups include methyl, ethyl, propyl, isopropyl, butyl, isobutyl, tertiary butyl, pentyl, hexyl and the like. An alkyl group may be optionally substituted with one or more substituents are selected from the group consisting of hydroxyl, cyano, alkoxy, =O, =S, $NO_2$, halogen, dimethyl amino, and SH.

As used herein, the term "alkenyl" means a straight-chain, branched or cyclic unsaturated hydrocarbon group containing at least one carbon-carbon double bond. For example, an alkenyl group can have 1 to 12 carbons, such as from 1 to 7 carbons, or from 1 to 4 carbons. An alkenyl group can optionally be substituted with one or more substituents. Exemplary substituents include hydroxyl, cyano, alkoxy, =O, =S, $NO_2$, halogen, dimethyl amino, and SH.

As used herein, the term "alkynyl" means a straight-chain, branched or cyclic unsaturated hydrocarbon containing at least one carbon-carbon triple bond. For example, an alkynyl group can have 1 to 12 carbons, such as from 1 to 7 carbons, or from 1 to 4 carbons. An alkynyl group can optionally be substituted with one or more substituents. Exemplary substituents include hydroxyl, cyano, alkoxy, =O, =S, $NO_2$, halogen, dimethyl amino, and SH.

As used herein, the term "alkoxyl" means an "O-alkyl" group.

As used herein, the term "aryl" means an aromatic group which has at least one ring having a conjugated pi electron system and includes carbocyclic aryl, heterocyclic aryl and biaryl groups. An aryl group can optionally be substituted with one or more subtituents. Exemplary substituents include halogen, trihalomethyl, hydroxyl, SH, OH, $NO_2$, amine, thioether, cyano, alkoxy, alkyl, and amino.

As used herein, the term "alkaryl" means an alkyl that is covalently joined to an aryl group. The alkyl can be, for example, a lower alkyl.

As used herein, the term "carbocyclic aryl" means an aryl group wherein the ring atoms are carbon.

As used herein, the term "heterocyclic aryl" means an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

As used herein, the term "hydrocarbyl" means a hydrocarbon radical having only carbon and hydrogen atoms. For example, an hydrocarbyl radical can have from 1 to 20 carbon atoms, such as from 1 to 12 carbon atoms or from 1 to 7 carbon atoms.

As used herein, the term "substituted hydrocarbyl" means a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

As used herein, the term "amide" means —C(O)—NH—R', wherein R' is alkyl, aryl, alkylaryl or hydrogen. As used herein, the term "thioamide" means —C(S)—NH—R', wherein R' is alkyl, aryl, alkylaryl or hydrogen. As used herein, the term "amine" means a —N(R")R''' group, wherein R" and R''' are independently selected from the group consisting of alkyl, aryl, and alkylaryl. As used herein, the term "thioether" means —S—R", wherein R" is alkyl, aryl, or alkylaryl. As used herein, the term "sulfonyl" refers to —S(O)$_2$—R'''', where R'''' is aryl, C(CN)=C-aryl, $CH_2CN$, alkyaryl, sulfonamide, NH-alkyl, NH-alkylaryl, or NH-aryl.

IV. Screening Assays

The ability of a compound to selectively reduce persistent sodium current relative to transient sodium current can be determined using a variety of assays. Such assays can be performed, for example, in a cell or tissue that expresses an endogenous or recombinantly expressed persistent sodium current, and generally involve determining persistent and transient sodium current prior to and following application of a test compound.

Methods for measuring sodium current are well known to those skilled in the art, and are described, see, e.g., Joseph S. Adorante, *Inhibition of Noninactivating Na Channels of Mammalian Optic Nerve as a Means of Preventing Optic Nerve Degeneration Associated with Glaucoma*, U.S. Pat. No. 5,922,746 (Jul. 13, 1999); Bert Sakmann & Erwin Neher, SINGLE CHANNEL RECORDING (Plenum Press, 2$^{nd}$ ed. 1995); and Tsung-Ming Shih et al., *High-level Expression and Detection of Ion Channels in Xenopus Oocytes*, 529-556 (METHODS IN ENZYMOLOGY: ION CHANNELS PART B, Vol. 293, P. Michael Conn ed., Academic Press 1998), which are hereby incorporated by reference in their entirety. These protocols are routine procedures well within the scope of one skilled in the art and from the teaching herein (see, e.g., Examples 1, 2, 3 and 4). Since the rate at which sodium currents open and close is rapid and the speed at which ions flow through the channel is high, channel function can be studied using an electrophysiological approach, which is capable of measuring the ion flux at the rate of one million ions per second with a millisecond time resolution. In addition, as shown in Examples 1, 2 and 3, a method for identifying a selective persistent sodium channel antagonist or other persistent sodium current antagonist can involve using a fluorescent dye that is sensitive to change in cell membrane potential in order to enable optical measurement of cell membrane potential. As disclosed herein below, a compound to be tested is added to a well containing cells that express a sodium channel capable of mediating a persistent sodium current, and express a potassium channel or a sodium/potassium ATPase or both.

Methods for measuring membrane potential with voltage-sensitive dyes are well known to those skilled in the art, and are described, see, e.g., Iain D. Johnson, *Fluorescent Probes for Living Cells* 30(3) HISTOCHEM. J. 123-140 (1998); and IMAGING NEURONS: A LABORATORY MANUAL (Rafael Yuste, et al., eds., Cold Spring Harbor Laboratory Press, 2000). In particular, the example listed below takes advantage of the high temporal and spatial resolution that derives from utilization of fluorescence resonance energy transfer (FRET) in the measurement of membrane potential by voltage-sensitive dyes as described, see, e.g., Jesus E. Gonzalez & Roger Y. Tsien, *Improved Indicators of Cell Membrane Potential That Use Fluorescence Resonance Energy Transfer* 4(4) CHEM. BIOL. 269-277 (1997); Roger Y. Tsien & Jesus E. Gonzalez, *Voltage Sensing by Fluorescence Resonance Energy Transfer*, U.S. Pat. No. 5,661,035 (Aug. 26, 1997); Roger Y. Tsien & Jesus E. Gonzalez, *Detection of Transmembrane Potentials by Optical Methods*, U.S. Pat. No. 6,342,379 (Jan. 29, 2002); Jesus E. Gonzalez & Michael P. Maher, *Cellular Fluorescent Indicators and Voltage/Ion Probe Reader (VIPR) Tools for Ion Channel and Receptor Drug Discovery*, 8(5-6) RECEPTORS CHANNELS 283-295, (2002); and Michael P. Maher & Jesus E. Gonzalez, *High Throughput Method and System for Screening Candidate Compounds for Activity Against Target Ion Channels*, U.S. Pat. No. 6,686,193 (Feb. 3, 2004), which are hereby incorporated by reference in their entirety.

In addition, the selectivity of a compound for persistent sodium current versus transient sodium current can be confirmed, as shown in the teaching herein (see, e.g., Examples 2 and 3).

A variety of cell types, including naturally occurring cells and genetically engineered cells can be used in an in vitro assay to detect persistent sodium current. Naturally occurring cells having non-inactivating sodium current include, for example, several types of neurons, such as squid axon, cerebellar Purkinje cells, neocortical pyramidal cells, thalamic neurons, CA1 hipppocampal pyramidal cells, striatal neurons and mammalian CNS axons. Other naturally occurring cells having persistent sodium current can be identified by those skilled in the art using methods disclosed herein below and other well known methods. Cells for use in testing a compound for its ability to alter persistent sodium current can be obtained from a mammal, such as a mouse, rat, pig, goat, monkey or human, or a non-mammal containing a cell expressing a sodium channel capable of mediating persistent sodium current.

Genetically engineered cells having persistent sodium current can contain, for example, a cDNA encoding a sodium channel capable of mediating a persistent current such as $Na_v1.3$; or can be a cell engineered to have increased expression of a sodium channel capable of mediating a persistent current, decreased expression of a sodium channel mediating a transient current, or both. Recombinant expression is advantageous in providing a higher level of expression of a sodium channel capable of mediating a persistent sodium current than is found endogenously and also allows expression in cells or extracts in which the channel is not normally found. One or more recombinant nucleic acid expression constructs generally contain a constitutive or inducible promoter of RNA transcription appropriate for the host cell or transcription-translation system, operatively linked to a nucleotide sequence that encodes one or more polypeptides of the channel of interest. The expression construct can be DNA or RNA, and optionally can be contained in a vector, such as a plasmid or viral vector. Based on well-known and publicly available knowledge of nucleic acid sequences encoding subunits of many sodium channels, including several sodium channels capable of mediating a persistent sodium current, one skilled in the art can express desired levels of a biologically active persistent or transient sodium channels using routine laboratory methods as described, see, e.g., Molecular Cloning A Laboratory Manual (Joseph Sambrook & David W. Russell eds., Cold Spring Harbor Laboratory Press, $3^{rd}$ ed. 2001); and CURRENT PROTOCOLS IN MOLECULAR BIOLOGY (Frederick M. Ausubel et al., eds., John Wiley & Sons, 2004), which are hereby incorporated by reference in their entirety. cDNAs for several families of sodium channels have been cloned and sequenced, and are described, see, e.g., Alan L. Goldin, *Diversity of Mammalian Voltage-gated Sodium Channels*, 868 ANN. N.Y. ACAD. SCI. 38-50 (1999), William A. Catterall, *From Ionic Currents to Molecular Mechanisms: The Structure and Function of Voltage-gated Sodium Channels*, 26(1) NEURON 13-25 (2000); John N. Wood & Mark D. Baker, *Voltage-gated Sodium Channels*, 1(1) CURR. OPIN. PHARMACOL. 17-21 (2001); and Frank H. Yu & William A. Catterall, *Overview of the Voltage-Gated Sodium Channel Family*, 4(3) GENOME BIOL. 207 (2003), which are hereby incorporated by reference in their entirety. In addition, both nucleotide and protein sequences all currently described sodium channels are publicly available from the GenBank database (National Institutes of Health, National Library of Medicine, http://www.ncbi.nlm.nih.gov/), which is hereby incorporated by reference in its entirety.

Exemplary host cells that can be used to express recombinant sodium channels include isolated mammalian primary cells; established mammalian cell lines, such as COS, CHO, HeLa, NIH3T3, HEK 293-T and PC12; amphibian cells, such as *Xenopus* embryos and oocytes; and other vertebrate cells. Exemplary host cells also include insect cells such as *Drosophila*, yeast cells such as *S. cerevisiae*, *S. pombe*, or *Pichia pastoris* and prokaryotic cells (such as *E. coli*,) engineered to recombinantly express sodium channels.

V. Reaction Schemes

A compound used in a method of the invention can be synthesized by general synthetic methodology, such as by the specific synthetic reaction schemes and methodologies described below and in Examples 5, 6, 7 and 8. Modifications of these synthetic methodologies will become readily apparent to the practicing synthetic organic chemist in view of the following disclosure and general knowledge available in the art.

The reaction schemes disclosed below are directed to the synthesis of exemplary compounds used in a method of the invention. The synthetic processes described herein are adaptable within the skill of the practicing organic chemist and can be used with such adaptation for the synthesis of compounds useful in a method of the invention that are not specifically described. Reaction schemes 1, 2, 3 and 4 disclose synthetic routes to compounds having Formulas 1, 2, 3 and 4, respectively. Examples 5, 6, 7 and 8 describe methodology useful for synthesizing exemplary compounds representative of Formulas 1, 2, 3 and 4, respectively.

The specific reaction conditions described in Examples 5, 6, 7 and 8 are directed to the synthesis of exemplary compounds useful in a method of the invention. Whereas each of the specific and exemplary synthetic methods shown in Examples 5, 6, 7 and 8 describe specific compounds within the scope of general Formulas 1 through 4, the synthetic processes and methods used therein are adaptable within the skill of the practicing organic chemist and can be used with such adaptation for the synthesis of compounds useful in a method of the invention that are not specifically described herein as examples.

Reaction scheme 1
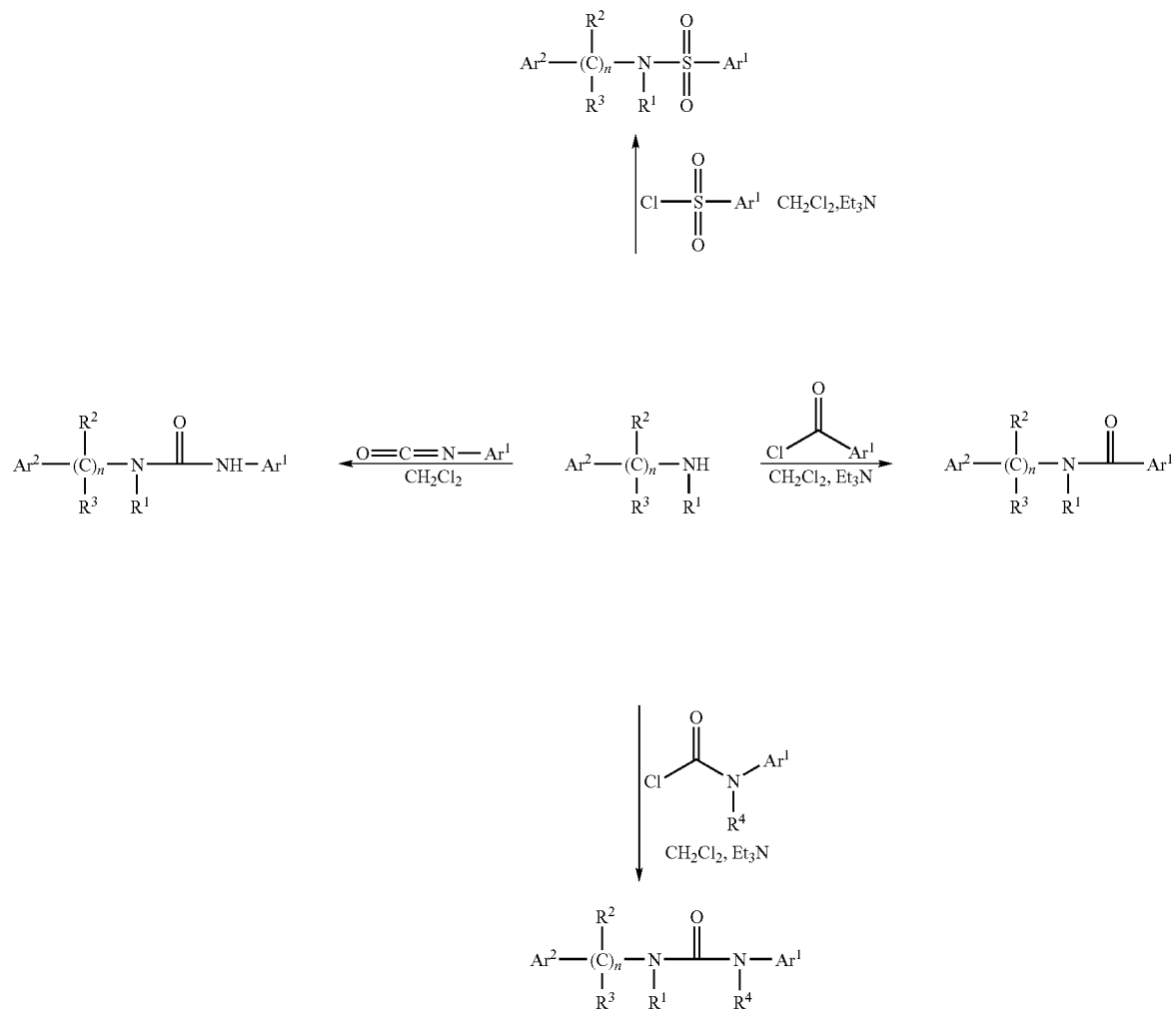
Reaction Scheme 2
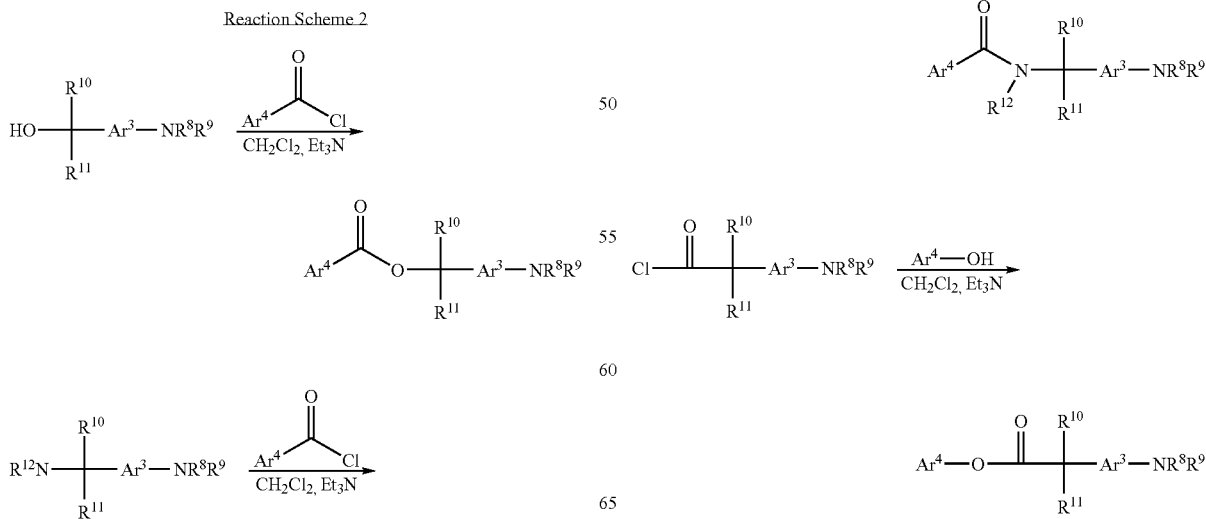

Reaction Scheme 3

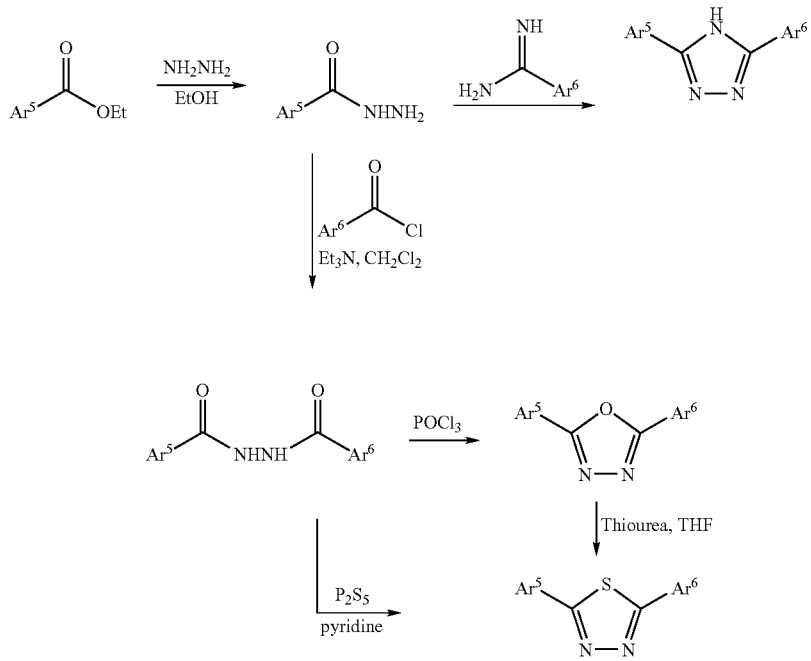

Reaction Scheme 4

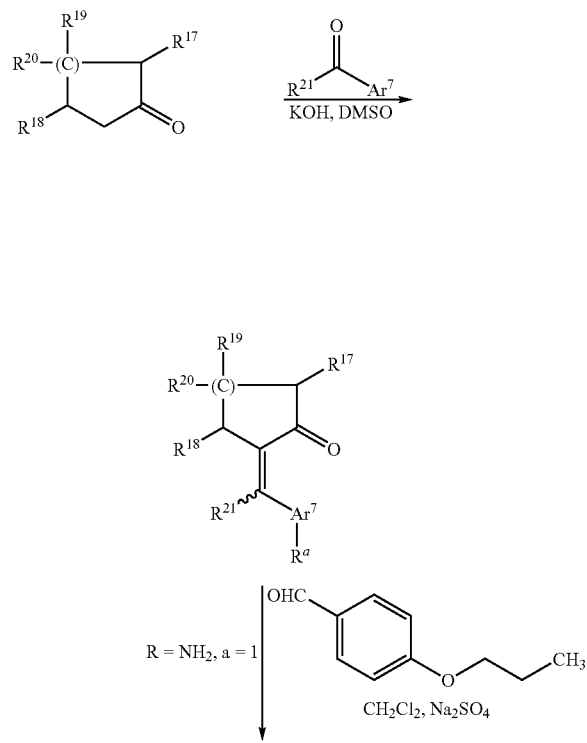

VI. Pain Models

The ability of a compound that selectively reduces persistent sodium current relative to transient sodium current to treat chronic pain in a mammal can be confirmed using a variety of well-known assays. Such essays include, but are not limited to, the Mouse Writhing Assay, the Tail Flick Assay, the Sciatic Nerve Ligation assay, the Formalin Test and the Dorsal Root Ganglia Ligation assay.

An accepted standard for detecting and comparing the analgesic activity of different classes of analgesic compounds for which there is a correlation with human analgesic activity is the prevention of acetic acid induced writhing in mice, see, e.g., R. Koster et al., *Acetic Acid for Analgesic Screening*, 18 FED. PROC. 412-416 (1959). In the Mouse Writhing Assay, mice are treated with various doses of a test compound or vehicle, followed by intraperitoneal injection with a standard challenge dose of acetic acid 5 minutes prior to a designated observation period. The acetic acid can be prepared as a 0.55% solution and injected at a volume of 0.1 ml/10 grams of body weight. For scoring purposes a "writhe" is indicated by whole body stretching or contracting of the abdomen during an observation period beginning about five minutes after the administration of acetic acid.

Another model that has been used to define or monitor analgesic levels following exposure to a variety of compounds is the Tail Flick Assay, see, e.g., William L. Dewey et al., *The Effect of Narcotics and Narcotic Antagonists on the Tail-Flick Response in Spinal Mice*, 21(8) J. PHARM. PHARMACOL. 548-550 (1969). In this assay, an apparatus can be used to test mice, rats or monkeys by focusing a beam of light on the tail and evaluating latency to tail-flick. This test has proven useful for screening weak and strong analgesics. In the Tail flick Assay, mice are treated with various doses of a test compound or vehicle. At a selected time point after administration, mice are placed in a holding tube and the time required for each mouse to react (tail flick) to the heat from a beam of light focused on the tail is recorded on a Tail Flick Apparatus (Columbus Instruments, Columbus, Ohio).

An accepted model for assessment of neuropathic pain analgesia is the Chung model of peripheral neuropathic pain, see, e.g., Sun H. Kim & Jin M. Chung, *An Experimental Model for Peripheral Neuropathy Produced by Segmental Spinal Nerve Ligation in the Rat*, 50(3) PAIN 355-363 (1992), which is hereby incorporated by reference in its entirety. The Chung model is a selective spinal neurectomy model that involves introducing partial nerve injury by performing a spinal nerve ligation procedure. These protocols for this procedure are routine and well within the scope of one skilled in the art and from the teaching herein (see, e.g., Example 4).

Another accepted model for assessment of neuropathic pain analgesia is the Sciatic Nerve Ligation model, see, e.g., Gary J. Bennett and Yi-Kuan Xie, *A Peripheral Mononeuropathy in Rat That Produces Disorders of Pain Sensation Like Those Seen in Man*, 33(1) PAIN 87-107 (1988); and Youn-Woo Lee et al., *Systemic and Supraspinal, but not Spinal, Opiates Suppress Allodynia in a Rat Neuropathic Pain Model*, 199(2) NEUROSCI. LETT. 186:111-114 (1995), which are hereby incorporated by reference in their entirety. In the Sciatic Nerve Ligation model, rats are anesthetized and a nerve ligation procedure performed. The common sciatic nerve is exposed and 4 ligatures are tied loosely around it with about 1 mm spacing. One day to 10 weeks after surgery, nociceptive testing is performed. Responses to noxious heat are determined by placing the rats in a chamber with a clear glass floor and aiming at the plantar surface of the affected foot a radiant heat source from beneath the floor. Increased latency to withdraw the hindpaw is demonstrative of analgesic activity. Responses to normally innocuous mechanical stimuli are determined by placing the rats in a chamber with a screen floor and stimulating the plantar surface of the hind paw with graduated von Frey hairs which are calibrated by the grams of force required to bend them. Rats with sciatic nerve ligation respond to lower grams of mechanical stimulation by reflexive withdrawal of the foot than unoperated rats, demonstrating allodynia. An increase in the grams of mechanical force required to produce foot withdrawal is demonstrative of anti-allodynic activity.

The Formalin Test is a well accepted model of inflammatory pain, see, e.g., Annika B. Malmberg & Tony L. Yaksh, *Antinociceptive Actions of Spinal Nonsteroidal Anti-Inflammatory Agents on the Formalin Test in the Rat*, 263(1) J. PHARMACOL. EXP. THER. 136-146 (1992). Rats are anesthetized, and, following a loss of spontaneous movement, they are injected subcutaneously in the dorsal surface of the hindpaw with 50 microliters of 5% formalin solution using a 30 gauge needle. Rats are then individually placed in an open Plexiglas chamber for observation, and within a maximum interval of 1 to 2 minutes, the animals display recovery from anesthesia with spontaneous activity and normal motor function. Pain behavior is quantified by periodically counting the incidents of spontaneous flinching/shaking of the injected paw. The flinches are counted for 1-minute periods at 1- to 2-, 5- to 6- and 5 minute intervals during the interval from 10 to 60 minutes. Inhibition of the flinching/shaking of the injected paw is demonstrative of an analgesic activity.

Using any of these assays, those skilled in the art recognize that $ED_{50}$ values and their standard errors of the mean can be determined using accepted numerical methods, see, e.g., Roger E. Kirk, EXPERIMENTAL DESIGN: PROCEDURES FOR THE BEHAVIORAL SCIENCES, (Wadsworth Publishing, $3^{rd}$ ed. 1994), which is hereby incorporated by reference in its entirety. One skilled in the art understands that any of the above or other well known models of pain can be useful for corroborating that a selective persistent sodium current antagonist, including a selective persistent sodium channel antagonist, is useful for treating chronic pain.

VII. Pharmaceutical Compositions

As disclosed herein, a selective persistent sodium current antagonist is administered to a mammal to treat chronic pain. As used herein, the term "treating chronic pain," when used in reference to administering to a mammal an effective amount of a selective persistent sodium current antagonist, means reducing a symptom of chronic pain, or delaying or preventing onset of a symptom of chronic pain in the mammal. For example, the term "treating chronic pain" can mean reducing a symptom of chronic pain by at least 30%, 40%, 60%, 70%, 80%, 90% or 100%. The effectiveness of a selective persistent sodium current antagonist in treating chronic pain can be determined by observing one or more clinical symptoms or physiological indicators associated with pain. For example, a reduction in chronic pain can include an arrest or a decrease in clinical symptoms of chronic pain or physiological indicators associated with chronic pain. A reduction in chronic pain also can be indicated by a reduced need for a concurrent therapy for chronic pain, such as reduced need for analgesic therapy, TENS, counterirritation, trigger point injection, spray and stretch, or physical therapy. Those of skill in the art will know the appropriate symptoms or indicators associated with specific types of chronic pain and will know how to determine if an individual is a candidate for treatment with a selective persistent sodium current antagonist.

The appropriate effective amount to be administered for a particular application of the methods can be determined by those skilled in the art, using the guidance provided herein. For example, an effective amount can be extrapolated from in vitro and in vivo assays as described herein above. One skilled in the art will recognize that the condition of the patient can be monitored throughout the course of therapy and that the effective amount of a selective persistent sodium current antagonist that is administered can be adjusted accordingly.

The invention also can be practiced by administering an effective amount of persistent sodium current antagonist together with one or more other agents including, but not limited to, one or more analgesic agents. In such "combination" therapy, it is understood that the antagonist can be delivered independently or simultaneously, in the same or different pharmaceutical compositions, and by the same or different routes of administration as the one or more other agents.

Exemplary compounds that have at least 20-fold selectivity for reducing persistent sodium current relative to non-persistent sodium current include those shown in Formulas 1, 2, 3 and 4. Also encompassed by the invention are pharmaceutically acceptable salts, esters and amides derived from Formulas 1, 2, 3 or 4. Suitable pharmaceutically acceptable salts of the antagonists useful in the invention include, without limitation, acid addition salts, which can be formed, for example, by mixing a solution of the antagonist with a solution of an appropriate acid such as hydrochloric acid, sulfuric acid, fumaric acid, maleic acid, succinic acid, acetic acid, benzoic acid, citric acid, tartaric acid, carbonic acid or phosphoric acid. Where an antagonist carries an acidic moiety, suitable pharmaceutically acceptable salts thereof can include alkali salts such as sodium or potassium salts; alkaline earth salts such as calcium or magnesium salts; and salts formed with suitable organic ligands, for example, quaternary ammonium salts. Representative pharmaceutically acceptable salts include, yet are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Thus, it is understood that the functional groups of antagonists useful in the invention can be modified to enhance the pharmacological utility of the compound. Such modifications are well within the knowledge of the skilled chemist and include, without limitation, esters, amides, ethers, N-oxides, and pro-drugs of the indicated antagonist. Examples of modifications that can enhance the activity of an antagonist include, for example, esterification such as the formation of C1 to C6 alkyl esters, such as C1 to C4 alkyl esters, wherein the alkyl group is a straight or branched chain. Other acceptable esters include, for example, C5 to C7 cycloalkyl esters and arylalkyl esters such as benzyl esters. Such esters can be prepared from the compounds described herein using conventional methods well known in the art of organic chemistry.

Other pharmaceutically acceptable modifications include the formation of amides. Useful amide modifications include, for example, those derived from ammonia; primary C1 to C6 dialkyl amines, where the alkyl groups are straight or branched chain; and arylamines having various substitutions. In the case of secondary amines, the amine also can be in the form of a 5- or 6-member ring. Methods for preparing these and other amides are well known in the art.

It is understood that, where an antagonist useful in the invention has at least one chiral center, the antagonist can exist as chemically distinct enantiomers. In addition, where an antagonist has two or more chiral centers, the compound exists as diastereomers. All such isomers and mixtures thereof are encompassed within the scope of the indicated antagonist. Similarly, where an antagonist possesses a structural arrangement that permits the structure to exist as tautomers, such tautomers are encompassed within the scope of the indicated antagonist. Furthermore, in crystalline form, an antagonist can exist as polymorphs; in the presence of a solvent, an antagonist can form a solvate, for example, with water or a common organic solvent. Such polymorphs, hydrates and other solvates also are encompassed within the scope of the indicated antagonist as defined herein.

A selective persistent sodium current antagonist or other compound useful in the invention generally is administered in a pharmaceutical acceptable composition. As used herein, the term "pharmaceutically acceptable" refer to any molecular entity or composition that does not produce an adverse, allergic or other untoward or unwanted reaction when administered to a human or other mammal. As used herein, the term "pharmaceutically acceptable composition" refers to a therapeutically effective concentration of an active ingredient. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition disclosed in the present specification can optionally include a pharmaceutically acceptable carriers that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, $7^{th}$ ed. 1999); REMINGTON: THE SCIENCE AND PRACTICE OF PHARMACY (Alfonso R. Gennaro ed., Lippincott, Williams & Wilkins, $20^{th}$ ed. 2000); GOODMAN & GILMAN's THE PHARMACOLOGICAL BASIS OF THERAPEUTICS (Joel G. Hardman et al., eds., McGraw-Hill Professional, $10^{th}$ ed. 2001); and HANDBOOK OF PHARMACEUTICAL EXCIPIENTS (Raymond C. Rowe et al., APhA Publications, $4^{th}$ edition 2003) which are hereby incorporated by reference in their entirety. These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE®. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

An antagonist useful in a method of the invention is administered to a mammal in an effective amount. Such an effective amount generally is the minimum dose necessary to achieve the desired therapeutic effect, which can be, for example, that amount roughly necessary to reduce the discomfort caused by the pain to tolerable levels or to achieve a significant reduction in pain. For example, the term "effective amount" when used with respect to treating chronic pain can be a dose sufficient to reduce pain, for example, by at least 30%, 40%, 50%, 60%, 70%, 80%, 90% or 100%. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the chronic pain, the age and weight of the patient, the patient's general physical condition, the cause of chronic pain and the route of administration. Where repeated administration is used, the frequency of administration depends, in part, on the half-life of the antagonist. Suppositories and extended release formulations can be useful in the invention and include, for example, dermal patches, formulations for deposit on or under the skin and formulations for intramuscular injection. It is understood that slow-release formulations also can be useful in the methods of the invention. The subject receiving the selective persistent sodium channel antagonist can be any mammal or other vertebrate capable of experiencing chronic pain, for example, a human, primate, horse, cow, dog, cat or bird.

Various routes of administration can be useful for treating chronic pain according to a method of the invention. A pharmaceutical composition useful in the methods of the invention can be administered to a mammal by any of a variety of means depending, for example, on the type and location of chronic pain to be treated, the antagonist or other compound to be included in the composition, and the history, risk factors and symptoms of the subject. Routes of administration suitable for the methods of the invention include both systemic and local administration. As non-limiting examples, a pharmaceutical composition useful for treating chronic pain can be administered orally or by subcutaneous pump; by dermal patch; by intravenous, subcutaneous or intramuscular injection; by topical drops, creams, gels or ointments; as an implanted or injected extended release formulation; as a bioerodable or non-bioerodable delivery system; by subcutaneous minipump or other implanted device; by intrathecal pump or injection; or by epidural injection. An exemplary list of biodegradable polymers and methods of use are described in, e.g., Heller, *Biodegradable Polymers in Controlled Drug Delivery* (CRC CRITICAL REVIEWS IN THERAPEUTIC DRUG CARRIER SYSTEMS, Vol. 1. CRC Press, 1987); Vernon G. Wong, *Method for Reducing or Preventing Transplant Rejection in the Eye and Intraocular Implants for Use Therefor*, U.S. Pat. No. 6,699,493 (Mar. 2, 2004); Vernon G. Wong & Mae W. L. Hu, *Methods for Treating Inflammation-mediated Conditions of the Eye*, U.S. Pat. No. 6,726,918 (Apr. 27, 2004); David A. Weber et al., *Methods and Apparatus for Delivery of Ocular Implants*, U.S. Patent Publication No. US2004/0054374 (Mar. 18, 2004); Thierry Nivaggioli et al., *Biodegradable Ocular Implant*, U.S. Patent Publication No. US2004/0137059 (Jul. 15, 2004), which are hereby incorporated by reference in their entirety. It is understood that the frequency and duration of dosing will be dependent, in part, on the relief desired and the half-life of the selective persistent sodium current antagonist.

In particular embodiments, a method of the invention is practiced by peripheral administration of a selective persistent sodium current antagonist. As used herein, the term "peripheral administration" or "administered peripherally" means introducing an agent into a subject outside of the central nervous system. Peripheral administration encompasses any route of administration other than direct administration to the spine or brain. As such, it is clear that intrathecal and epidural administration as well as cranial injection or implantation are not within the scope of the term "peripheral administration" or "administered peripherally." It further is clear that some selective persistent sodium current antagonists can cross the blood-brain barrier and, thus, become distributed throughout the central and peripheral nervous systems following peripheral administration.

Peripheral administration can be local or systemic. Local administration results in significantly more of a pharmaceutical composition being delivered to and about the site of local administration than to regions distal to the site of administration. Systemic administration results in delivery of a pharmaceutical composition to essentially the entire peripheral nervous system of the subject and may also result in delivery to the central nervous system depending on the properties of the composition.

Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

It is understood that modifications which do not substantially affect the activity of the various embodiments of this invention are also included within the definition of the invention provided herein. Accordingly, the following examples are intended to illustrate but not limit the present invention.

EXAMPLES

Example 1

High-Throughput Screening Assay for Identification of Inhibitors of Persistent Sodium Current To identify compounds that inhibit persistent sodium current, a primary high-throughput screen was employed, see, e.g., Joseph S. Adorante et al., *High-throughput Screen for Identifying Channel Blockers that Selectively Distinguish Transient from Persistent Sodium Channels*, U.S. Patent Publication No. 2002/0077297 (Jun. 20, 2002), which is hereby incorporated by reference in its entirety.

I. Compound Identification Assay Overview

To examine the ability of test compounds to alter persistent sodium current, human embryonic kidney (HEK) cells were transfected with $Na_v1.3$ sodium channel to obtain cells that express sodium current capable of mediating persistent sodium current. HEK cells expressing $Na_v1.3$ (HEK-$Na_v1.3$) were added to assay plate wells containing a $Na^+$-free media and physiologic concentrations of $K^+$ (4.5 mM) and preincubated for 20 minutes with ion-sensitive FRET dyes and either 5 µM of a test compound or a DMSO control. The assay plates were then transferred to a voltage/ion probe reader (VIPR) (Aurora Biosciences, San Diego, Calif.) and the VIPR was adjusted so that the fluorescent emission ratio from the donor ands acceptor FRET dyes equaled 1.0. To elicit persistent sodium current, a double addition protocol was performed by first adding an isotonic solution to adjust the concentration of sodium and potassium ions in the well to 110 mM and 10 mM, respectively, and measuring the resulting sodium-dependent depolarization and second by adding $K^+$ to a final concentration of 80 mM, and measuring $K^+$-dependent depolarization. Test compounds that block the $Na^+$ dependent signal, but not the $K^+$ dependent signal were selected for further analysis. The $Na^+$-dependent depolarization resulting from the persistent $Na^+$ was measured as shown in FIG. 2. The labeled boxes indicate the application of $Na^+$ or $K^+$. Circles indicate the control response with 0.1% DMSO added, triangles show the effects of the $Na^+$ channel inhibitor tetracaine (10 µM), and the diamonds show the response during the application of a non-specific channel blocker.

In this high-throughput assay, non-specific agents that inhibit membrane depolarizations induced by any effector must be distinguished from true persistent $Na^+$ current antagonists, which block only $Na^+$-dependent depolarizations. Therefore, a counter-screen to determine the ability of compounds to alter $K^+$-dependent depolarization was performed. As shown in FIG. 2, following pre-incubation with vehicle alone (DMSO) both $Na^+$ and $K^+$ additions produced a robust depolarization as indicated by the increase in Rf/Ri. Tetracaine, a $Na^+$ channel blocker, inhibited the $Na^+$-dependent, but not the $K^+$-dependent change in Rf/Ri. In contrast, a non-specific inhibitor of $Na^+$ and $K^+$-dependent depolarization blocked the change in Rf/Ri following either addition. This data demonstrates that selective antagonists of the persistent sodium current can be identified using the described method.

To eliminate compounds that non-specifically inhibited the $Na^+$-dependent depolarization, data obtained using the above procedure was analyzed with respect to a counter-screen that used $K^+$-dependent depolarization as a readout. To select hits from the primary screen, the data were plotted as histograms. Inhibition of the $Na^+$-dependent depolarization was plotted against inhibition of the $K^+$-dependent depolarization. Based on these data, the criteria for selection as a hit, was a greater or equal to 90% inhibition of the $Na^+$-dependent depolarization and a less than or equal to 20% inhibition of the $K^+$-dependent depolarization. This protocol provided a distinction between compounds that were inert or non-specific in their effects and compounds that specifically block the persistent sodium current.

II. Solutions

Solution compositions and volumes used in the assay are described below. Functions of some components of the solutions using the assay are as follows: (1) CC2-DMPE: a stationary coumarin-tagged phospholipid resonance energy donor. This dye is excited at 405 nm wavelength light and in the absence FRET emits fluorescence at 460 nm. (2) DiSBAC2 (3) or DiSBAC6(3): mobile resonance energy acceptors that partition across the membrane as a function of the electric field. The excitation spectra for these dyes overlap the emission of the coumarin donor and, thus, they act as FRET acceptors. They have an emission spectrum in the range of 570 nm. (3) ESS-AY17: reduces the background fluorescence that complicates the assay. (4) $CdCl_2$ (400 µM) was included in the pre-incubation solutions to stabilize the membrane potential of the cells at negative resting potential, resulting in the maximum number of $Na^+$ channels being available for activation. (5) Extracellular Cl— was replaced with $MeSO_3$ during preincubation and throughout the assay. This eliminates a complicating Cl— current during the assay and results in an amplified and more stable voltage-change induced by the persistent $Na^+$ current. (6) 1st $K^+$ addition: functions to depolarize the test cells to a voltage that activates substantial numbers of $Na^+$ channels. (7) 2nd $K^+$ addition: this addition produces a $K^+$-dependent depolarization, which is used as a counterscreen to eliminated non-specific blockers.

III. Cell Culture

HEK-293 cells were grown in Minimum Essential Medium (Invitrogen, Inc., Carlsbad, Calif.) supplemented with 10% Fetal Bovine Serum (Invitrogen, Inc., Carlsbad, Calif.) and 1% Pennicillin-Streptomycin (Invitrogen, Inc., Carlsbad, Calif.). Medium for HEK-$Na_v1.3$ cells also contained 500 mg/ml G418 Geneticin (Invitrogen, Inc., Carlsbad, Calif.) and 2 µM TTX (Calbiochem, Inc., San Diego, Calif.) for maintaining selective pressure. Cells were grown in vented cap flasks, in 90% humidity and 10% $CO_2$, to about 80% confluence and generally split by trypsinization 1:5 or 1:10.

HEK-$Na_v1.3$ cells were seeded in 96-well plates (Becton-Dickinson, San Diego, Calif.) coated with Matrigel (Becton-Dickinson, San Diego, Calif.) at 40,000 cells (in 100 µl culture medium) per well, and assayed the following day (16-20 hours). Cells were sometimes incubated in 96-well plates at somewhat lower densities (20,000 per well), and incubated for up to 40-48 hours.

IV. HEK-$Na_v1.3$ Handling and Dye Loading

Approximately 16 to 24 hours before the assay, HEK-$Na_v1.3$ cells were seeded in 96-well poly-lysine coated plates at 40,000 per well. On the day of the assay, medium was aspirated and cells were washed 3 times with 150 uL of Bath Solution #1 (BS#1) using CellWash (Thermo LabSystems, Franklin, Mass.).

A 20 µM CC2-DMPE solution was prepared by mixing coumarin stock solution with 10% Pluronic 127 1:1 and then dissolving the mix in the appropriate volume of BS#1. After the last wash, 50 ml of 20 µM CC2-DMPE solution was added to 50 mL of residual bath in each well to make 10 µM coumarin staining buffer. Plates were incubated in the dark for 30-60 minutes at room temperature.

While the cells were being stained with coumarin, a 10 µM DiSBAC2(3) solution in TEA-MeSO3 bath was prepared. In addition to oxonol, this solution contained any drug(s) being tested, at 4 times the desired final concentration (e.g. 20 µM for 5 µM final), 1.0 mM ESS-AY17, and 400 µM $CdCl_2$.

After 30-60 minutes of CC2-DMPE staining, the cells were washed 3 times with 150 µL of TEA-MeSO$_3$ buffer. Upon removing the bath, the cells were loaded with 80 µL of the DiSBAC2(3) solution and incubated for 20-30 minutes as before. Typically, wells in one column on each plate (e.g. column 11) were free of test drug(s) and served as positive and negative controls.

Once the incubation was complete, the cells were ready to be assayed on VIPR for sodium addback. 240 µL of NaMeSO3 buffer was added to stimulate the cells, resulting in a 1:4 dilution of the drugs; 240 µL of TEA-MeSO$_3$ buffer or 1 µM TTX was used as a positive control.

V. VIPR Instrumentation and Data Process

Optical experiments in microtiter plates were performed on the Voltage/Ion Probe Reader (VIPR) using two 400 nm excitation filters and filter sticks with 460 nm and 570 nm filters on the emission side for the blue and red sensitive PMTs, respectively. The instrument was run in column acquisition mode with 2 or 5 Hz sampling and 30 seconds of recording per column. Starting volumes in each well were 80 ml; usually 240 mL was added to each well during the course of the experiment. The lamp was allowed to warm up for about 20 minutes, and power to the PMTs was turned on for about 10 minutes prior to each experiment.

Ratiometric measurements of changes in fluorescent emissions at 460- and 570 nm on the VIPR platform (Aurora Bioscience, San Diego, Calif.) demonstrated that this assay format produces a robust and reproducible fluorescent signal upon depolarization of HEK-Na$_v$1.3 cells with a Na$^+$/K$^+$ addition. From a normalized ratio of 1.0 in Na$^+$-free media, Na$^+$-dependent depolarization resulted in an increase in the 460/570 ratio to over 2.2 (FIG. 2). Inter-well analysis of the ratios indicated that the amplitude of signal was large enough and consistent enough to be used in high-throughput screening.

Data were analyzed and reported as normalized ratios of intensities measured in the 460 nm and 580 nm channels. The VIPR sampling rate varied between 2 and 5 Hz in different experiments, with 5 Hz used for higher resolution of the peak sodium responses. The process of calculating these ratios was performed as follows. On all plates, column 12 contained TEA-MeSO$_3$ buffer with the same DiSBAC2(3) and ESS-AY17 concentrations as used in the cell plates; however no cells were included in column 12. Intensity values at each wavelength were averaged for the duration of the scan. These average values were subtracted from intensity values in all assay wells. The initial ratio obtained from samples 5-10 (Ri) was defined as:

$$Ri = \frac{\text{Intensity}_{460\,nm, samples\,5-10} - \text{background}_{460\,nm}}{\text{Intensity}_{580\,nm, samples\,5-10} - \text{background}_{580\,nm}}$$

and the ratio obtained from sample f (Rf) was defined as:

$$Rf = \frac{\text{Intensity}_{460\,nm, sample\,f} - \text{background}_{460\,nm}}{\text{Intensity}_{580\,nm, sample\,f} - \text{background}_{580\,nm}}$$

Final data were normalized to the starting ratio of each well and reported as Rf/Ri. The fluorescent response in the Na$_v$1.3 persistent current assay reached a peak approximately 10 seconds following the start of the run, therefore, the maximum ratio was selected as the readout for the assay (FIG. 3).

VI. Assay Reproducibility and Resolution

The assay format described above allows for quality assurance by measuring both negative (DMSO 0.1%) and positive (tetracaine 10 µM) controls. Every 10th plate in an assay run was a control plate. The data from these plates were used to verify that the assay conditions were optimal and to normalize the data from the test compounds. FIG. 3 shows results from control plates from multiple assays.

Figure 3A:
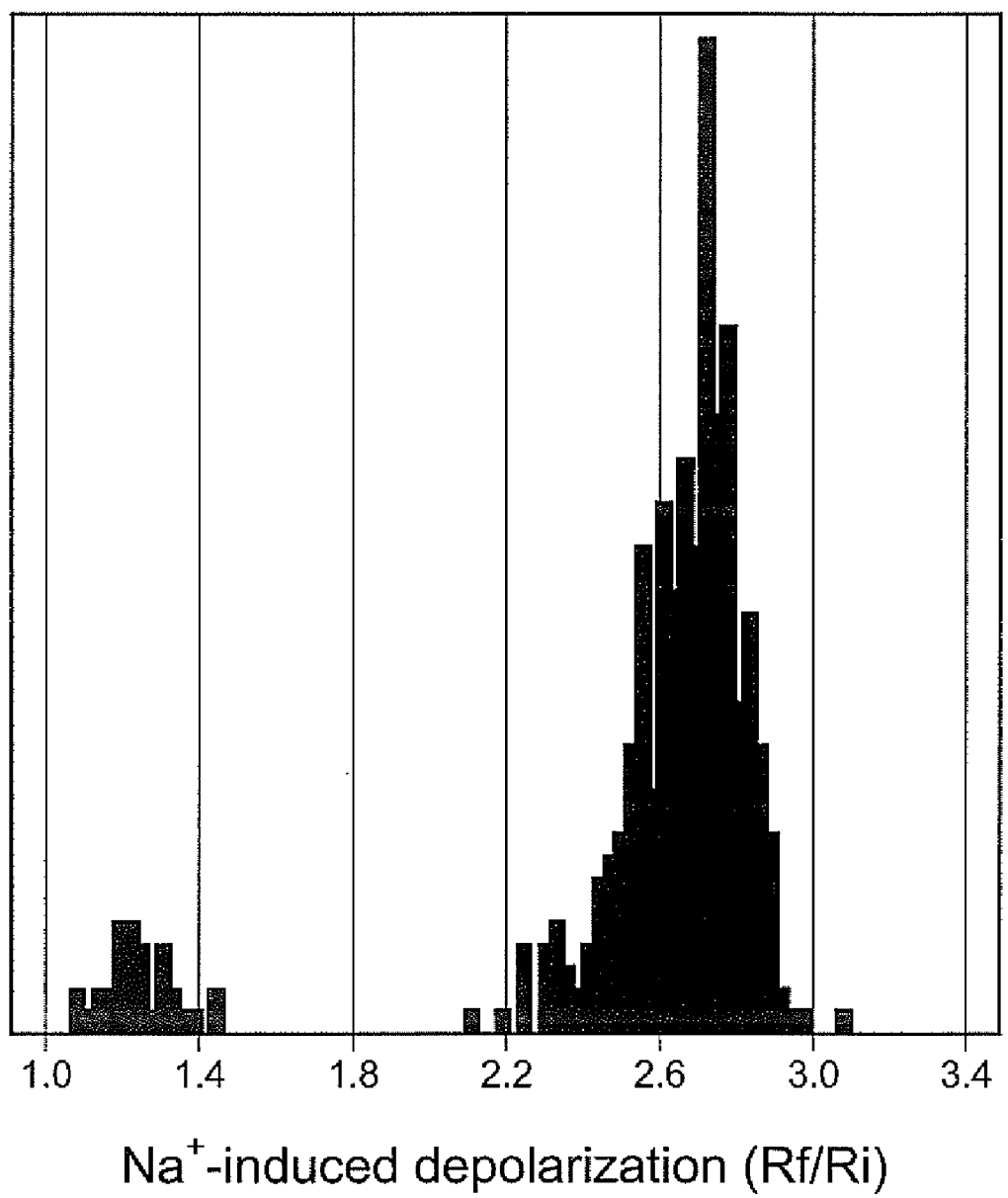
FIG. 3 shows data from assays in which the screening window for the persistent current assay is determined. To evaluate the size of the "screening window," data was examined from assays in which responses to sodium-dependent depolarization were measured in the presence of 10 µM Tetracaine to completely block the sodium-dependent depolarization or in the presence of a 0.1% DMSO control to obtain a maximum depolarization. Data were binned into histograms and a screening window (Z) was calculated from the mean and standard deviation for the maximal and minimum values according to the equation: $Z=1-(3\times STD_{Max}+3\times STD_{Min})/(Mean_{Max}-Mean_{Min})$. Histograms A, B and C represent data obtained from three different assay plates. The screening window for a run was considered adequate $1.0 \geq Z \geq 0.5$.
Figure 3B:
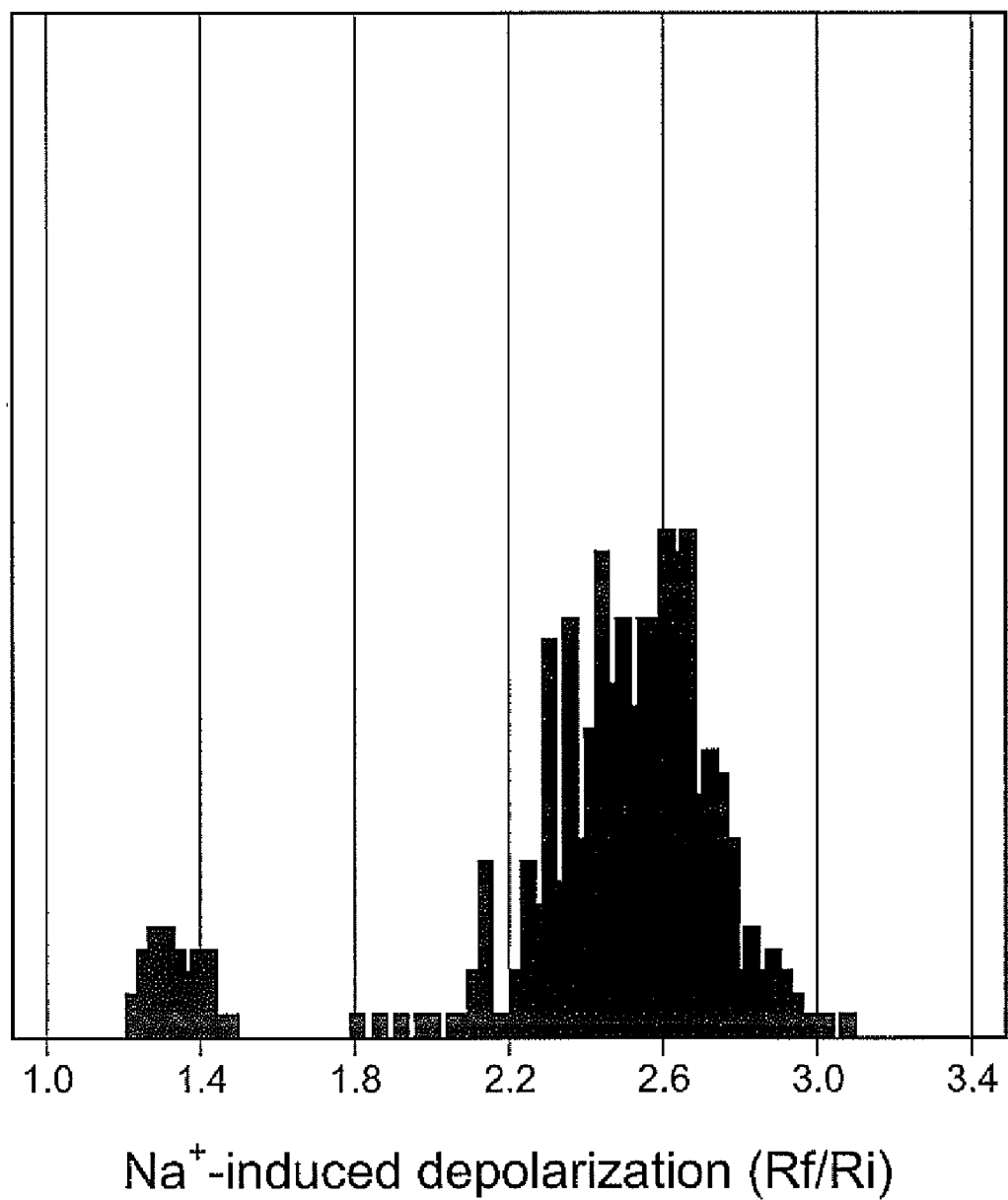
Figure 3C:
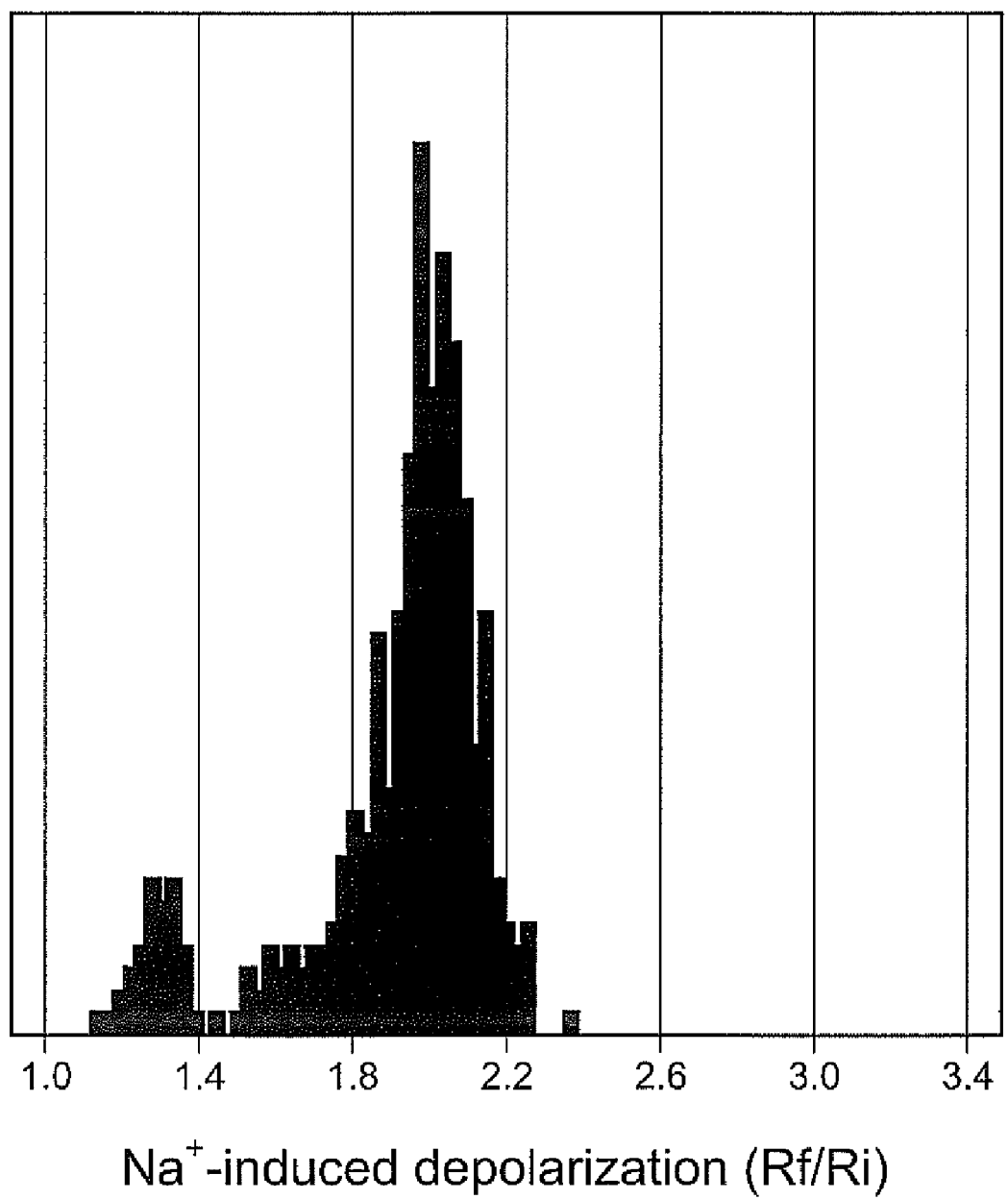

In FIG. 3, control plates having wells containing either 0.1% DMSO or 10 µM tetracaine were run after every ninth assay plate. The response to Na$^+$-dependent depolarization was measured and the data were binned into histograms as shown. The mean maximum response (Max) obtained in the presence of (0.1% DMSO) and the mean minimum response (Min) obtained in the presence of 10 µM tetracaine were determined. For quality control, data variance was compared to the difference between the maximum and minimum signals. This was accomplished by calculating a screening window (z) for each control plate. Data for the run was accepted if $1.0 \geq 2$ $Z \geq 20.5$.

$$Z = 1 - \frac{3 \times STD_{max} + 3 \times STD_{min}}{\text{Mean}_{max} - \text{Mean}_{min}}$$

Example 2

Moderate-Throughput Screening Assay for Selectivity of Inhibitors of Persistent Sodium Current Compounds obtained by the high-throughput screening described in Example 1 were tested for selectivity of blockade of persistent sodium current with respect to blockade of transient sodium current using a moderate-throughput screen. The selectivity assay utilizes Estim technology (Aurora Bioscience, San Diego, Calif.) to induce channel activation. This assay has an inherently greater time resolution than the high-throughput assay, and thus allows the measurement of both the transient and persistent components of the Na$^+$ currents within a single experiment.

I. Compound Selectivity Assay Overview

The Estim technology involves instrumenting 96-well plates with electrodes so that application of an appropriate voltage gradient across the well (electric field stimulation, EFS) can be used for activation of the ion channels in the target cells. EFS of HEK-293 cells expressing Na$_v$1.3 channels resulted in a rapid depolarization followed by a delayed repolarization. The transient Na$^+$ current drives the rapid depolarization while the persistent Na$^+$ current sustains the delayed repolarization. When similar experiments were performed in cells expressing channels that do not exhibit persistent currents, only rapid depolarization was seen. For quantification of the block of transient current, the amplitude of peak response was averaged for seven stimuli. The average response was converted to activity by normalizing against the difference between the responses in Ringer's solution with DMSO and Ringer's solution containing 10 µM tetracaine. Persistent current activity was calculated by integrating under the curve. The area obtained for each compound was normalized against the responses obtained with the DMSO control and in the presence of 10 µM tetracaine.

II. Cell Culture

Approximately 16 to 24 hours before the assay, HEK-Na$_v$1.3 cells were seeded in 96-well poly-lysine coated plates at 60,000 per well. On the day of the assay, medium was aspirated were cells were washed 3 times with 150 µL of HBSS using CellWash (Thermo LabSystems, Franklin, Mass.).

III. HEK-Na$_v$1.3 Handling and Dye Loading

A 20 µM CC2-DMPE solution was prepared by mixing coumarin stock solution with 10% Pluronic 127 1:1 and then dissolving the mix in the appropriate volume of HBSS. After the last wash, 50 µL of 20 µM CC2-DMPE solution was added to 50 µL of residual bath in each well to make 10 µM coumarin staining buffer. Plates were incubated in the dark for 30 minutes at room temperature.

While the cells were being stained with CC2-DMPE, a 0.2 µM DiSBAC6(3) solution in HBSS was prepared.

After 30 minutes of CC2-DMPE staining, the cells were washed 3 times with 150 µL of HBSS. After the last wash, 50 µL of 0.2 µM DiSBAC6(3) solution was added to 50 µL of residual bath in each well to make 0.1 µM oxonol staining buffer. Plates were then incubated in the dark for 15 minutes.

After 15 minutes of DiSBAC6(3) staining, the cells were washed again 3 times with 150 µL of HBSS. After the last wash, 50 µL of 1.0 µM ESS-AY17 solution was added to 50 µL of residual bath in each well to make 0.5 µM ESS. This solution also contained any drug(s) being tested, at twice the desired final concentrations. Plates were incubated in the dark again for 15 minutes. Once the incubation was complete, the cells were assayed on EFS/VSP reader.

III. Fast FRET Reader Instrumentation and Data Process

Optical experiments in microtiter plates were performed on the fast FRET Reader using two 400 nm excitation filters and filter sticks with 460 nm and 580 nm filters on the emission side for the blue and red sensitive PMTs, respectively. The instrument was run in column acquisition mode with 100 Hz sampling and 12 seconds of recording per column. Seven pulses were applied at 1 Hz, starting at 2 seconds. The lamp was allowed to warm up for about 20 minutes, and power to the PMTs was turned on for about 10 minutes prior to each experiment.

Data were analyzed and reported as normalized ratios of intensities measured in the 460 nm and 580 nm channels. The process of calculating these ratios was performed as follows. On all plates, column 12 contained HBSS with the same ESS-AY17 concentration as used in the cell plates; however no cells were included in column 12. Intensity values at each wavelength were averaged for the duration of the scan. These average values were subtracted from intensity values in all assay wells. The initial ratio obtained from samples 50-100 (Ri) was defined as:

$$Ri = \frac{\text{Intensity}_{460\,nm,\,samples\,50\text{-}100} - \text{background}_{460\,nm}}{\text{Intensity}_{580\,nm,\,samples\,50\text{-}100} - \text{background}_{580\,nm}}$$

and the ratio obtained from sample f (Rf) was defined as:

$$Rf = \frac{\text{Intensity}_{460\,nm,\,sample\,f} - \text{background}_{460\,nm}}{\text{Intensity}_{580\,nm,\,sample\,f} - \text{background}_{580\,nm}}$$

Data were normalized to the starting ratio of each well and reported as Rf/Ri. The transient Na$^+$-current signal was calculated as average of the peaks resulting from the seven electric pulses applied in the course of recording. The persistent Na$^+$-current signal was calculated integrating the area under the total response during the seven electric pulses applied in the course of recording. Selectivity was determined by comparison of concentrations of agent required to block 50% of the persistent current (IC$_{50}$) vs. the IC$_{50}$ for the transient current.

Example 3

Electrophysiological Assay for Selectivity of Inhibitors of Persistent Sodium Current To confirm the blocking selectivity of test compounds for persistent sodium current, individual compounds were examined using a whole-cell patch clamp method.

HEK cells transfected with Na$_v$1.3 sodium channels that express transient and persistent sodium currents were plated onto glass coverslips and cultured in MEM cell culture media with Earle's salts and GlutaMAX (Invitrogen, Inc., Carlsbad, Calif.) supplemented with:10% Fetal bovine serum, heat inactivated (Invitrogen, Inc., Carlsbad, Calif.), 0.1 mM MEM non-essential amino acids (Invitrogen, Inc., Carlsbad, Calif.), 10 mM HEPES (Invitrogen, Inc., Carlsbad, Calif.), 1% Penicillin/Streptomycin (Invitrogen, Inc., Carlsbad, Calif.).

After an incubation period of from 24 to 48 hours the culture medium was removed and replaced with external recording solution (see below). Whole cell patch clamp experiments were performed using an EPC10 amplifier (HEKA Instruments, Lambrecht, Germany.) linked to an IBM compatible personal computer equipped with PULSE software. Borosilicate glass patch pipettes were pulled to a fine tip on a P90 pipette puller (Sutter Instrument Co., Novato, Calif.) and were polished (Microforge, Narishige, Japan) to a resistance of about 1.5 Mohm when filled with intracellular recording solution (Table 1).

TABLE 1

Patch Clamp Solutions

| External Recording Solution | | Internal Recording Solution | |
| --- | --- | --- | --- |
| Compound | Concentration | Compound | Concentration |
| NaCl | 127 mM | CsMeSO$_3$ | 125 mM |
| HEPES (free acid) | 10 mM | CsCl | 25 mM |
| KCl | 5 mM | NaHEPES | 10 mM |
| CsCl | 5 mM | Amphotericin | 240 µg/ml |
| Glucose | 10 mM | | |
| MgCl$_2$ | 0.6 mM | | |
| CaCl$_2$ | 1.2 mM | | |
| CdCl$_2$ | 200 µM | | |
| pH to 7.4 with NaOH @ room temp. 290 mOsm. | | pH 7.20 with CsOH 300 mOsm | |

Persistent and transient currents in HEK cells expressing Na$_v$1.3 channels were measured by applying 200-msec depolarizations from a holding potential of −90 mV to 0 mV. Background currents that remained in the presence of 500 nM TTX were subtracted from all traces. Drugs were perfused directly into the vicinity of the cells using a microperfusion system.

Figure 4:
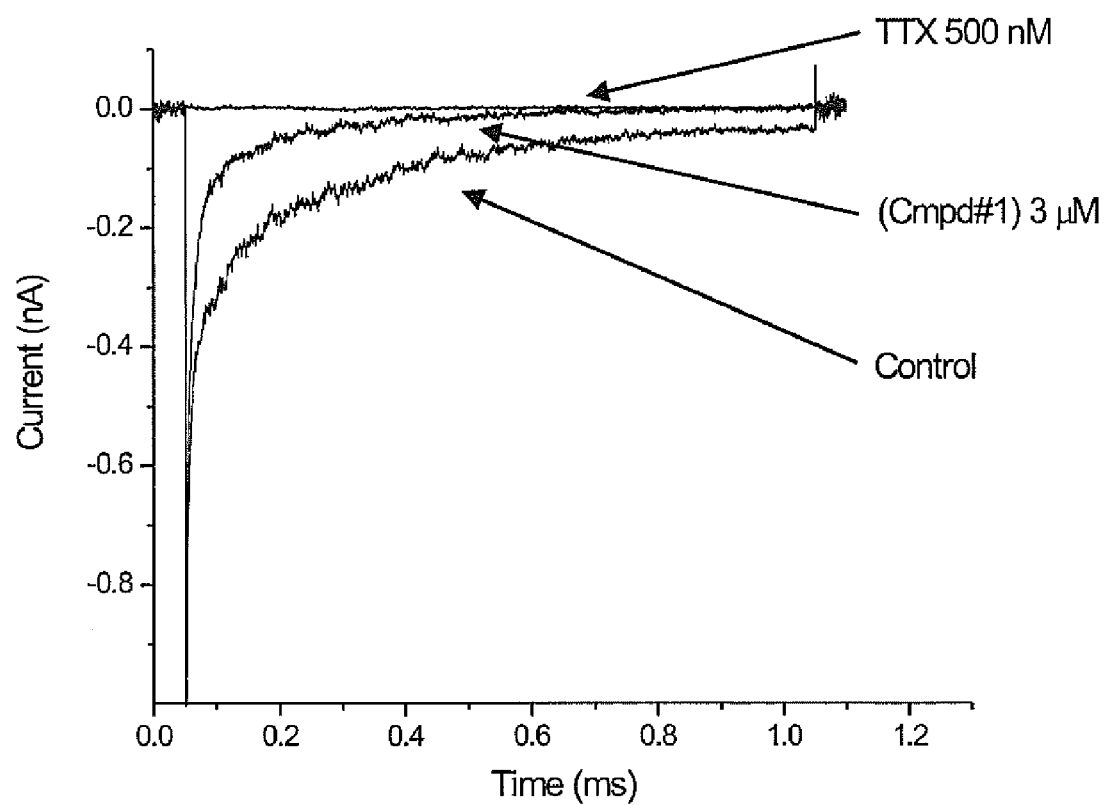
FIG. 4 shows sodium current traces before and after the addition of 3 µM Compound 1 or 500 nM TTX. HEK cells expressing Na$_v$1.3 channels were patch clamped in the perforated-patch mode. Currents were elicited by 200 msec test pulses to 0 mV from a holding potential of –90 mV.
Figure 5:
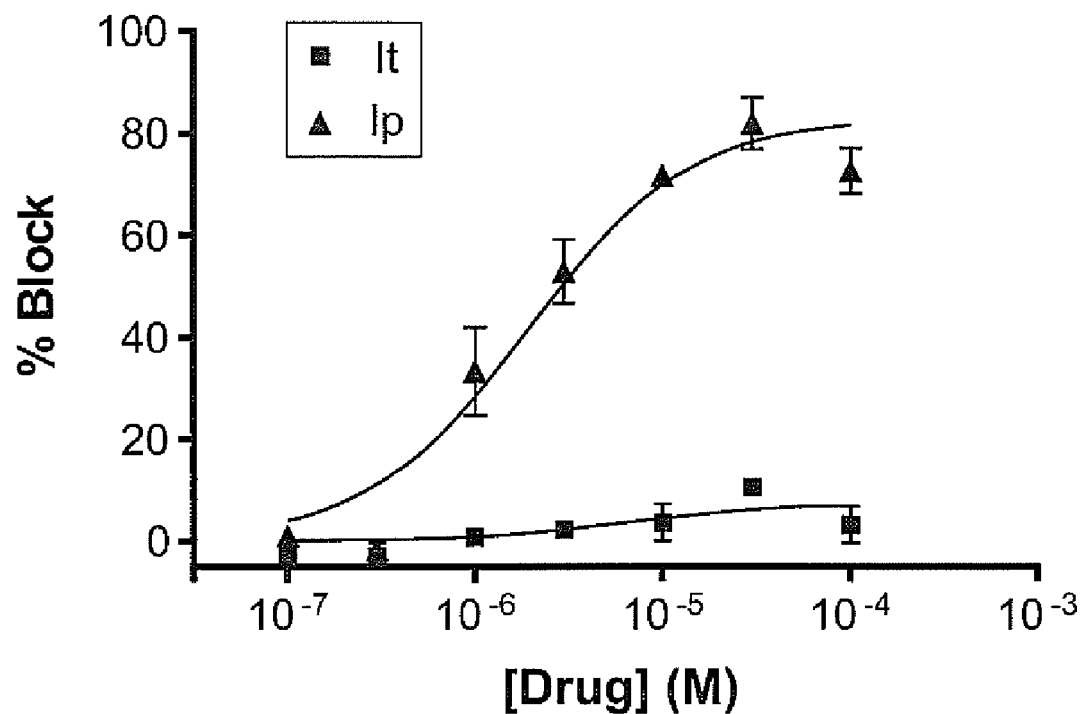
FIG. 5 shows a dose-response curve for Compound 1. The peak amplitudes of transient Na$^+$ current ($I_t$) and the steady state amplitude of the persistent current ($I_p$) were measured at various Compound 1 concentrations, normalized to amplitude of the control currents. The percent block was then plotted against drug concentration. Solid lines represent fits to the data with the Hill equation. The calculated EC$_{50}$ values and Hill coefficients are as follows: Hillslope, $I_t$ is 0.354 and $I_p$ is 0.733; EC$_{50}$, $I_t$ is 0.167 M and $I_p$ is $3.71\times10^{-6}$ M.

Under control conditions, depolarizing pulses elicited a large transient inward current that declined to a smaller persistent current, which remained stable during the remainder of the pulse (FIG. 4, control). Addition of 500 nM TTX completely blocked both the transient and persistent currents (FIG. 4, TTX). Application of 3 µM of Compound 1, produced a much different effect. Inspection of FIG. 4 reveals that the Compound 1 blocked 99% of the persistent current while only reducing the transient current by 16%. Dose-response analysis for Compound 1 demonstrates its significant selectivity for blocking the persistent sodium current relative to the transient sodium current over a four order of magnitude range (FIG. 5).

Example 4

Administering a Selective Persistent Sodium Current Antagonist in a Rodent Model Results in Reduced Pain This example describes reversal of allodynia in an animal model of neuropathic pain by administering a selective persistent sodium channel antagonist.

Figure 6:
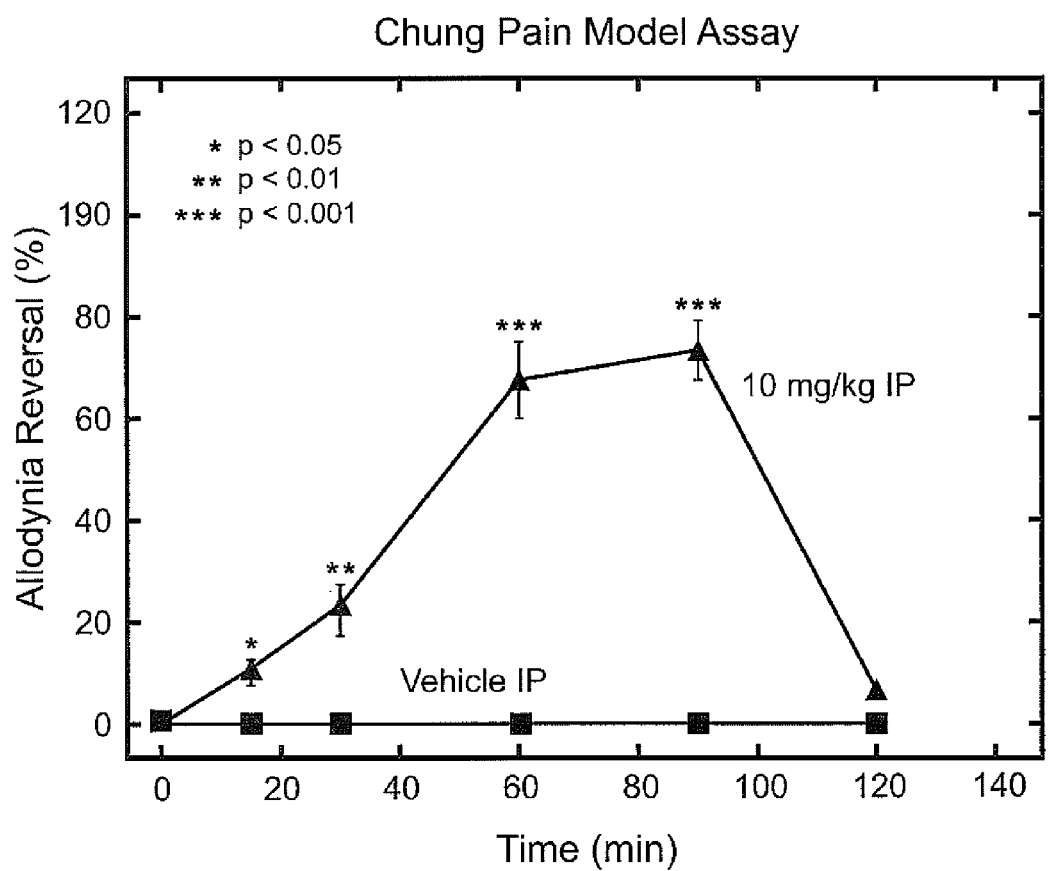
FIG. 6 shows the effects of intraperitoneally administered Compound 1 on paw withdrawal threshold (mean±SEM) in a test of mechanical allodynia in the spinal nerve ligation model of neuropathic pain. Paw withdrawal threshold (gram force) was determined using von Frey filament stimulation and the Dixon's up-down method. Allodynic response was measured at baseline (0 min) and at 15, 30, 60 and 120 min after of 10 mg/kg IP injection of Compound 1 or vehicle control. Percent reversal of allodynia compared with non-injected rats was calculated. Six rats were used at each dose. Data were analyzed by analysis of variance and Dunnett's test reversal of allodynia was considered significant if $P<0.05$

Compound 1 was tested in a rodent model of neuropathic pain known to be predictive of clinical activity, see, e.g., Kim & Chung, supra, (1992). Following ligation of two spinal nerves, the animals developed sensitivity to normally non-painful stimuli such as touch. The ability of Compound 1 to reverse this sensitivity, called allodynia, was tested 30 minutes after dosing by intraperitoneal administration. As shown in FIG. 6, Compound 1 produced an 80% reduction in allodynia with respect to a vehicle control.

The animal model used involved the surgical ligation of the L5 (and optionally the L6) spinal nerves on one side in experimental animals. Rats recovering from the surgery gained weight and displayed a level of general activity similar to that of normal rats. However, these rats developed abnormalities of the foot in which the hindpaw was moderately everted and the toes were held together. More importantly, the hindpaw on the side affected by the surgery became sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats were anesthetized before surgery. The surgical site was shaved and prepared either with betadine or Novacaine. Incision was made from the thoracic vertebra XIII down toward the sacrum. Muscle tissue was separated from the spinal vertebra (left side) at the L4-S2 levels. The L6 vertebra was located and the transverse process was carefully removed with a small rongeur to expose the L4-L6 spinal nerves. The L5 and L6 spinal nerves were isolated and tightly ligated with 6-0 silk thread. The same procedure was performed on the right side as a control, except that no ligation of the spinal nerves was performed.

A complete hemostasis was confirmed, then the wounds were sutured. A small amount of antibiotic ointment was applied to the incised area, and the rat was transferred to the recovery plastic cage under a regulated heat-temperature lamp. On the day of the experiment, at least seven days after the surgery, six rats per test group were administered the test drugs by intraperitoneal (i.p.) injection. For i.p. injection, Compound #1 was formulated in approximately 50% DMSO and given in a volume of 1 ml/kg body weight. Compound #1 was tested 10 mg/kg.

Tactile allodynia was measured prior to and 30 minutes after drug administration using von Frey hairs, which are a series of fine hairs with incremental differences in stiffness. Rats were placed in a plastic cage with a wire mesh bottom and allowed to acclimate for approximately 30 minutes. The von Frey hairs were applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair.

In summary, results shown in this example indicate that a selective persistent sodium current antagonist can be used to effectively reduce pain in a mammal.

Example 5

Synthesis of Exemplary Compounds Representative of Formula 1

A compound having general Formula 1, exemplified by thiophene-2-carboxylic acid (4-phenyl-butyl)-amide (Compound 1; FIG. 1) can be prepared as follows. A solution of thiophene-2-carbonyl chloride (147 mg, 1.0 mmol), triethylamine (101 mg, 1.0 mmol) in dichloromethane is treated with 4-phenylbutylamine (149 mg, 1.0 mmol). The reaction mixture is stirred until no further reaction occurs and is quenched by the addition of aqueous $NaHCO_3$ solution. The organic phase is collected and concentrated to give the title compound.

Example 6

Synthesis of Exemplary Compounds Representative of Formula 2

A compound having general Formula 2, exemplified by 1-Benzyl-4-(5-phenyl-[1,3,4]oxadiazol-2-yl)-pyridine (Compound 2; FIG. 1) can be prepared as follows. A solution of 4-(5-phenyl-[1,3,4]oxadiazol-2-yl)-pyridine (223 mg, 1.0 mmol) is prepared by the method of H. Smith Broadbent, et al., *Quinoxalines. I. Preparation and Stereochemistry of Decahydroquinoxalines*, 82(1) J. AMER. CHEM. SOC. 189-193 (1960) in chloroform is treated with benzylbromide (171 mg, 1.0 mmol). The reaction is stirred until no further reaction occurs. The reaction mixture is concentrated to give the title compound.

Example 7

Synthesis of Exemplary Compounds Representative of Formula 3

A compound having general Formula 3, exemplified by 6-Isopropyl-3-methyl-2-{4-[(4-propoxy-benzylidene)-amino]-benzylidene}-cyclohexanone (Compound 3; FIG. 1) can be prepared as follows. A solution of menthone (154 mg, 1.0 mmol) and 4-aminobenzaldehyde (121 mg, 1.0 mmol) in dimethylsulfoxide is treated with potassium hydroxide (56 mg, 1.0 mmol). The reaction is stirred until no futher reaction occurs. The reaction mixture is poured into ethyl acetate and water. The organic phase is collected, dried and concentrated to give 2-(4-Amino-benzylidene)-6-isopropyl-3-methyl-cyclohexanone. The 2-(4-Amino-benzylidene)-6-isopropyl-3-methyl-cyclohexanone is dissolved in dichloromethane and treated with 4-propoxybenzaldehyde (164 mg, 1.0 mmol) and anhydrous $Na_2SO_4$. The reaction mixture is stirred until no further reaction occurs. The reaction mixture is filtered and concentrated to give the title compound.

Example 8

Synthesis of Exemplary Compounds Representative of Formula 4

A compound having general Formula 4, exemplified by 3-(2,2,2-Trifluoro-acetylamino)-benzoic acid 2-oxo-2-phenyl-ethyl ester (Compound 4; FIG. 1) can be prepared as follows. A solution of 3-aminobenzoic acid (137 mg, 1.0 mmol) in dichloromethane is treated with trifluoroacetic anhydride (420 mg, 2.0 mmol). The reaction mixture is stirred until no further reaction occurs. The reaction mixture is concentrated to give 3-(2,2,2-Trifluoro-acetylamino)-benzoic acid. A solution of 3-(2,2,2-Trifluoro-acetylamino)-benzoic acid (233 mg, 1.0 mmol) and 2-hydroxyacetophenone (136 mg, 1.0 mmol) in dimethylformamide and diisopropylethylamine (260 mg, 2.0 mmol) is treated with HBTU (379 mg, 1.0 mmol). The reaction mixture is stirred until no further reaction occurs. The reaction is poured into ethyl acetate and water. The organic phase is collected, dried and concentrated to give the title compound.

Example 9

Oral Administration of a Persistent Sodium Current Blocker to Treat Neuropathic Pain from Trigeminal Neuralgia This example shows a method of persistent sodium current blocker (PSCB) therapy using a pharmaceutically acceptable composition comprising a PSCB compound to treat a neuralgic pain. While the example illustrates the use of a PSCB to treat trigeminal neuralgia, any acute spasmodic pain that travels along one or more nerves, such as, e.g., post-herpetic neuralgia, glossopharyngeal neuralgia, sciatica and atypical facial pain, can also be treated using this method.

A patient presents pain symptoms that are diagnosed as trigeminal neuralgia. She describes the pain as a sudden sharp stabbing pain on the right side of her face, eyes and lips. The pain is triggered when she tries to chew her food while eating and each episode lasts for several seconds and may repeat many times over the course of the day. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 10

Oral Administration of a Persistent Sodium Current Blocker to Treat Neuropathic Pain from Phantom Pain This example shows a method of persistent sodium current blocker (PSCB) therapy using a pharmaceutically acceptable composition comprising a PSCB compound to treat a deafferentation pain syndrome. While the example illustrates the use of a PSCB to treat phantom pain, any pain resulting from a loss of the sensory input from a portion of the body, such as, e.g., an injury to the brain, spinal cord, or a peripheral nerve, post-stroke pain, phantom pain, paraplegia, brachial plexus avulsion and postherpetic neuralgia, can also be treated using this method.

A patient with an amputated right arm presents symptoms that are diagnosed as phantom pain. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 11

Oral Administration of a Persistent Sodium Current Blocker to Treat Neuropathic Pain from Chemotherapy Treatment This example shows a method of persistent sodium current blocker (PSCB) therapy using a pharmaceutically acceptable composition comprising a PSCB compound to treat a polyneuropathic pain. While the example illustrates the use of a PSCB to treat pain induced from chemotherapy treatment, any pain involving two or more peripherial nerves, such as, e.g., diabetic neuropathy, treatment-induced pain, postmastectomy syndrome. post-polio syndrome, diabetes, alcohol, amyloid, toxins, HIV, hypothyroidism, uremia, vitamin deficiencies, 2',3'-didexoycytidine (ddC) treatment and Fabry's disease, can also be treated using this method.

A cancer patient undergoing chemotherapy presents symptoms that are diagnosed as chemotherapy-induced pain. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 12

Oral Administration of a Persistent Sodium Current Blocker to Treat Allodynia

This example shows a method of persistent sodium current blocker (PSCB) therapy using a pharmaceutically acceptable composition comprising a PSCB compound to treat allodynia.

A patient presents pain symptoms that are diagnosed as allodynia. She indicates that whenever something gently touches her lest forearm, she feels an intense pain like a sudden burning sensation. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 13

Oral Administration of a Persistent Sodium Current Blocker to Treat Hyperalgesia This example shows a method of persistent sodium current blocker (PSCB) therapy using a pharmaceutically acceptable composition comprising a PSCB compound to treat hyperalgesia.

A patient presents pain symptoms that are diagnosed as hyperalgesia. He indicates that whenever he mildly bumps his right thigh against a hard object, like a table corner, a great shooting pain occurs to such an extent that he needs to sit down. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 14

Oral Administration of a Persistent Sodium Current Blocker to Treat Hyperpathia

This example shows a method of persistent sodium current blocker (PSCB) therapy using a pharmaceutically acceptable composition comprising a PSCB compound to treat hyperpathia.

A patient presents pain symptoms that are diagnosed as hyperpathia. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 15

Oral Administration of a Persistent Sodium Current Blocker to Treat Chronic Pain from a Migraine Headache Pain This example shows a method of persistent sodium current blocker (PSCB) therapy using a pharmaceutically acceptable composition comprising a PSCB compound to treat pain from a headache. While the example illustrates the use of a PSCB to treat pain resulting from a migraine Headache, any headache pain, such as, e.g., tension-type headache, cluster headache, hormone headache, rebound headache, sinus headache and organic headache, can also be treated using this method.

A patient presents pain symptoms that are diagnosed as resulting from a migraine headache. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 16

Oral Administration of a Persistent Sodium Current Blocker to Treat Pain Associated with Rheumatoid Arthritis This example shows a method of persistent sodium current blocker (PSCB) therapy using a pharmaceutically acceptable composition comprising a PSCB compound to treat chronic pain resulting from inflammatory disorder. While the example illustrates the use of a PSCB to treat chronic pain resulting from a rheumatoid arthritis, any inflammatory disorder-induced pain, such as, e.g., osteoarthritis, gouty arthritis, spondylitis or autoimmune diseases such as lupus erythematosus, can also be treated using this method.

A patient presents pain symptoms that are diagnosed as resulting from rheumatoid arthritis. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 17

Oral Administration of a Persistent Sodium Current Blocker to Treat Chronic Back Pain This example shows a method of persistent sodium current blocker (PSCB) therapy using a pharmaceutically acceptable composition comprising a PSCB compound to treat chronic pain resulting from excessive muscle tension. While the example illustrates the use of a PSCB to treat chronic lower back pain, any excessive muscle tension-induced pain can also be treated using this method.

A patient presents with a non-spasmodic muscle pain localized at the lumbar region of the back due to a herniated disc. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 18

Oral Administration of a Persistent Sodium Current Blocker to Pain Associated with Treat Irritable Bowel Syndrome This example shows a method of persistent sodium current blocker (PSCB) therapy using a pharmaceutically acceptable composition comprising a PSCB compound to treat pain resulting from chronic gastrointestinal inflammations. While the example illustrates the use of a PSCB to treat the pain associated with irritable bowel syndrome, any gastrointestinal inflammation-induced pain, such as, e.g., Crohn's disease, ulcerative colitis and gastritis, can also be treated using this method.

A patient presents pain symptoms that are diagnosed as resulting from irritable bowel syndrome. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 19

Oral Administration of a Persistent Sodium Current Blocker to Treat Post-Operative Pain This example shows a method of persistent sodium current blocker (PSCB) therapy using a pharmaceutically acceptable composition comprising a PSCB compound to treat post-operative pain.

A patient presents pain symptoms resulting from a surgical operation. That patient is treated orally with a therapeutically-effective amount of a pharmaceutically acceptable composition comprising a PSCB. Within one day after the administration of a PSCB therapy, the patient's pain is substantially alleviated. Administration of the PSCB composition continues for about 1 to about 4 weeks to maintain this pain relief.

Example 20

Oral Administration of a Persistent Sodium Current Blocker to Treat Pain Associated with Fibromyalgia This example shows a method of persistent sodium current blocker (PSCB) therapy using a pharmaceutically acceptable composition comprising a PSCB compound to treat pain associated with fibromyalgia.

A patient presents pain symptoms that are diagnosed as resulting from fibromyalgia. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Example 21

Oral Administration of a Persistent Sodium Current Blocker to Treat Pain Associated with Repetitive Motion Disorder of the Wrist This example shows a method of persistent sodium current blocker (PSCB) therapy using a pharmaceutically acceptable composition comprising a PSCB compound to treat pain resulting from repetitive motion disorders (RMDs). While the example illustrates the use of a PSCB to treat the pain associated with RMDs of the wrist, any RMD-induced pain occurring in, e.g., hands, elbows, shoulders, neck, back, hips, knees, feet, legs, and ankles, can also be treated using this method.

A patient presents pain symptoms that are diagnosed as resulting from an RMD of the wrist. That patient is treated orally with a therapeutically-effective amount of a pharmaceutically acceptable composition comprising a PSCB. Within one day after the administration of a PSCB therapy, the patient's pain is substantially alleviated. Repeated administration of the PSCB composition maintains this pain relief.

Although the present invention has been described with reference to the disclosed embodiments, one skilled in the art will readily appreciate that the specific experiments disclosed are only illustrative of the present invention. Various modifications can be made without departing from the spirit of the present invention.

What is claimed:

1. A method of treating a neuropathic pain in a mammal, comprising administering to said mammal an effective amount of a selective persistent sodium channel antagonist, wherein said antagonist has at least 20-fold selectivity for a persistent sodium current relative to a transient sodium current, and wherein said antagonist is a compound included in formula 4, or a pharmaceutically acceptable salt, ester, amide, stereoisomer or racemic mixture thereof:

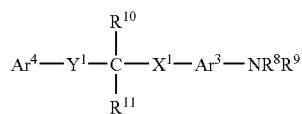

wherein
$Ar^3$ is phenyl or a substituted phenyl;
$Ar^4$ is phenyl or a substituted phenyl;
$X^1$ is absent or selected from the group consisting of

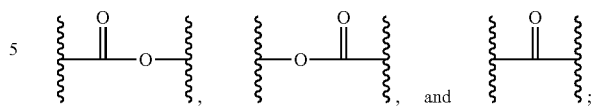

$Y^1$ is absent or selected from the group consisting of

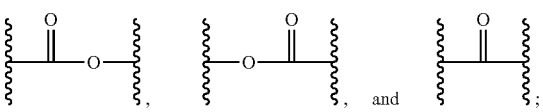

$R^8$ and $R^9$ are independently selected from the group consisting of hydrogen, $COCF_3$ and a $C_1$ to $C_8$ alkyl;
$R^{10}$ and $R^{11}$ are independently selected from the group consisting of hydrogen, hydroxy, halogen, and a $C_1$ to $C_8$ alkyl.

2. The method of claim 1, wherein said persistent sodium current is $Na_v1.1$ persistent current.

3. The method of claim 1, wherein said persistent sodium current is $Na_v1.2$ persistent current.

4. The method of claim 1, wherein said persistent sodium current is $Na_v1.3$ persistent current.

5. The method of claim 1, wherein said persistent sodium current is $Na_v1.5$ persistent current.

6. The method of claim 1, wherein said persistent sodium current is $Na_v1.6$ persistent current.

7. The method of claim 1, wherein said persistent sodium current is $Na_v1.7$ persistent current.

8. The method of claim 1, wherein said persistent sodium current is $Na_v1.8$ persistent current.

9. The method of claim 1, wherein said persistent sodium current is $Na_v1.9$ persistent current.

10. The method of claim 1, wherein said mammal is a human.

11. The method of claim 1, wherein said antagonist has at least 50-fold selectivity for said persistent sodium current relative to said transient sodium current.

12. The method of claim 1, wherein said antagonist has at least 200-fold selectivity for said persistent sodium current relative to said transient sodium current.

13. The method of claim 1, wherein said antagonist has at least 400-fold selectivity for said persistent sodium current relative to said transient sodium current.

14. The method of claim 1, wherein said antagonist has at least 600-fold selectivity for said persistent sodium current relative to said transient sodium current.

15. The method of claim 1, wherein said antagonist has at least 1000-fold selectivity for said persistent sodium current relative to said transient sodium current.

16. The method of claim 1, wherein said antagonist is administered peripherally.

17. The method of claim 1, wherein said antagonist is administered systemically.

18. The method of claim 1, wherein said antagonist is administered orally.

19. The method of claim 1, wherein said antagonist is administered in a sustained release formula.

20. The method of claim 1, wherein said antagonist is administered in a bioerodible delivery system.

21. The method of claim 1, wherein said antagonist is administered in a non-bioerodible delivery system.

22. The method of claim 1, wherein said $Ar^3$ is phenyl.

23. The method of claim 1, wherein said $Ar^3$ is a substituted phenyl.

24. The method of claim 23, wherein said substituted phenyl is substituted with one or more of halogen, a $C_1$ to $C_8$ alkyl, $NO_2$, $CF_3$, $OCF_3$, $OCF_2H$, CN, or $(CR^5R^6)_cN(R^7)_2$ wherein,
- $R^5$ and $R^6$ are independently selected from the group consisting of hydrogen, hydroxy, fluoro, and a $C_1$ to $C_8$ alkyl;
- $R^7$ is selected from the group consisting of hydrogen, and a $C_1$ to $C_8$ alkyl; and
- c is 0, 1, 2, 3, 4, or 5.

25. The method of claim 1, wherein said $Ar^4$ is phenyl.

26. The method of claim 1, wherein said $Ar^4$ is a substituted phenyl.

27. The method of claim 26, wherein said substituted phenyl is substituted with one or more of halogen, a $C_1$ to $C_8$ alkyl, $NO_2$, $CF_3$, $OCF_3$, $OCF_2H$, CN, or $(CR^5R^6)_cN(R^7)_2$ wherein,
- $R^5$ and $R^6$ are independently selected from the group consisting of hydrogen, hydroxy, fluoro, and a $C_1$ to $C_8$ alkyl;
- $R^7$ is selected from the group consisting of hydrogen, and a $C_1$ to $C_8$ alkyl; and
- c is 0, 1, 2, 3, 4, or 5.

28. The method of claim 1, wherein said $R^8$ is hydrogen, methyl, ethyl, propyl, or isopropyl.

29. The method of claim 1, wherein said $R^9$ is hydrogen, methyl, ethyl, propyl, or isopropyl.

30. The method of claim 1, wherein said $R^{10}$ is hydrogen, methyl, ethyl, propyl, or isopropyl.

31. The method of claim 1, wherein said $R^{11}$ is hydrogen, methyl, ethyl, propyl, or isopropyl.

32. The method of claim 22, wherein said antagonist is 3-(2,2,2-Trifluoro-acetylamino)-benzoic acid 2-oxo-2-phenyl-ethyl ester.

33. The method of claim 25, wherein said antagonist is

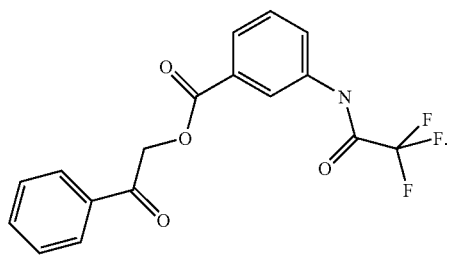

34. The method of claim 1, wherein said neuropathic pain is a neuralgia.

35. The method of claim 34, wherein said neuralgia is selected from the group consisting of a trigeminal neuralgia, a post-herpetic neuralgia, a glossopharyngeal neuralgia, a sciatica and an atypical facial pain.

36. The method of claim 1, wherein said neuropathic pain is a deafferentation pain syndrome.

37. The method of claim 36, wherein said deafferentation pain syndrome is selected from the group consisting of an injury to the brain or spinal cord, a post-stroke pain, a phantom pain, a paraplegia, a peripheral nerve injury, a brachial plexus avulsion injury and a lumbar radiculopathy.

38. The method of claim 1, wherein said neuropathic pain is a complex regional pain syndrome (CRPS).

39. The method of claim 38, wherein said complex regional pain syndrome is selected from the group consisting of a reflex sympathetic dystrophy (CRPS Type I) and a causalgia (CRPS Type II).

40. The method of claim 1, wherein said neuropathic pain is a polyneuropathic pain.

41. The method of claim 40, wherein said complex regional pain syndrome is selected from the group consisting of a diabetic neuropathy, a chemotherapy-induced pain, a treatment-induced pain, and a postmastectomy syndrome.

42. The method of claim 1, wherein said neuropathic pain is a centrally-generated neuropathic pain.

43. The method of claim 42, wherein said centrally-generated neuropathic pain is selected from the group consisting of a dorsal root ganglion compression, an inflammation of the spinal cord, a contusion, a tumor of the spinal cord, a hemisection of the spinal cord, a tumor of the brainstem, a tumor of the thalamus, a tumor of the cortex, a trauma of the brainstem, a trauma of the thalamus and a trauma of the cortex.

44. The method of claim 1, wherein said neuropathic pain is a peripherially-generated neuropathic pain.

45. The method of claim 44, wherein said peripherially-generated neuropathic pain is selected from the group consisting of a neuroma, a nerve compression, a nerve crush, a nerve stretch, a nerve entrapment and an incomplete nerve transsection.

46. The method of claim 1, wherein said neuropathic pain is an allodynia, a hyperalgesia and a hyperpathia.

47. The method of claim 1, wherein said effective amount reduces the symptoms of neuropathic pain by at least 30%.

48. The method of claim 1, wherein said effective amount reduces the symptoms of neuropathic pain by at least 50%.

49. The method of claim 1, wherein said effective amount reduces the symptoms of neuropathic pain by at least 70%.

50. The method of claim 1, wherein said effective amount reduces the symptoms of neuropathic pain by at least 90%.

* * * * *

UNITED STATES PATENT AND TRADEMARK OFFICE
CERTIFICATE OF CORRECTION

PATENT NO. : 7,763,651 B2
APPLICATION NO. : 11/461520
DATED : July 27, 2010
INVENTOR(S) : George R. Ehring et al.

It is certified that error appears in the above-identified patent and that said Letters Patent is hereby corrected as shown below:

In column 1, line 66, delete "phenyloin," and insert -- phenytoin --, therefor.

In column 4, line 66, delete "$R^{13}$," and insert -- $R^{18}$ --, therefor.

In column 5, line 9, delete "steroisomer," and insert -- stereoisomer, --, therefor.

In column 6, line 10, delete "05" and insert -- 05. --, therefor.

In column 7, line 2, delete "Tubermammillary" and insert -- Tuberomammillary --, therefor.

In column 7, line 45, delete "Ca2+" and insert -- $Ca^{2+}$ --, therefor.

In column 8, line 64, delete "phenyloin)" and insert -- phenytoin) --, therefor.

In column 10, line 33, delete "peripherially" and insert -- peripherally --, therefor.

In column 11, line 16, delete "didexoycytidine" and insert -- dideoxycytidine --, therefor.

In column 11, line 57, delete "orangic" and insert -- organic --, therefor.

In column 14, line 3, delete "steroisomer," and insert -- stereoisomer, --, therefor.

In column 15, line 65, delete "$(CR^5R^6)N(R^7)_2$" and insert -- $(CR^5R^6)_CN(R^7)_2$ --, therefor.

In column 15, line 67, delete "$(CR^5R^6)N(R^7)_2$" and insert -- $(CR^5R^6)_CN(R^7)_2$ --, therefor.

In column 16, line 2, delete "$(CR^5R^6)N(R^7)_2$" and insert -- $(CR^5R^6)_CN(R^7)_2$ --, therefor.

In column 16, line 15, delete ""$(CR^5R^6)_CN(R^7)_2$" and insert -- $(CR^5R^6)_CN(R^7)_2$, --, therefor.

In column 16, line 53, delete "$R^1$" and insert -- $R^{18}$ --, therefor.

In column 17, line 51, delete "subtituents." and insert -- substituents. --, therefor.

In column 18, line 20-21, delete "alkyaryl," and insert -- alkylaryl, --, therefor.

In column 19, line 29, delete "hipppocampal" and insert -- hippocampal --, therefor.

In column 27, line 46, delete "C1 to C6" and insert -- $C_1$ to $C_6$ --, therefor.

In column 27, line 46, delete "C1 to C4" and insert -- $C_1$ to $C_4$ --, therefor.

Signed and Sealed this

Fourteenth Day of September, 2010

David J. Kappos
*Director of the United States Patent and Trademark Office*

CERTIFICATE OF CORRECTION (continued)
U.S. Pat. No. 7,763,651 B2

In column 27, line 48, delete "C5 to C7" and insert -- $C_5$ to $C_7$ --, therefor.

In column 27, line 54, delete "C1 to C6" and insert -- $C_1$ to $C_6$ --, therefor.

In column 32, line 43, delete "Pennicillin" and insert -- Penicillin --, therefor.

In column 33, line 6, delete "MeSO3" and insert -- $MeSO_3$ --, therefor.

In column 33, line 20, delete "NaMeSO3" and insert -- $NaMeSO_3$ --, therefor.

In column 38, line 67, delete "futher" and insert -- further --, therefor.

In column 40, line 25, delete "peripherial" and insert -- peripheral --, therefor.

In column 40, line 29, delete "didexoycytidine" and insert -- dideoxycytidine --, therefor.

In column 43, line 65, in claim 1, delete "wherein" and insert -- wherein, --, therefor.

In column 45, line 40-50, in claim 33, delete " 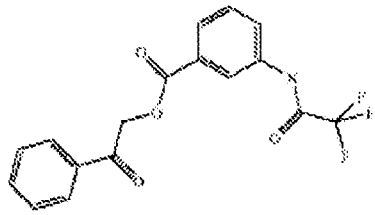 " and insert

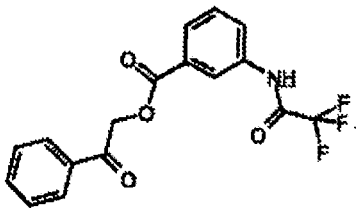

-- --, therefor.

In column 46, line 36, in claim 44, delete "peripherially" and insert -- peripherally --, therefor.

In column 46, line 37, in claim 45, delete "peripherially" and insert -- peripherally --, therefor.